(12) United States Patent
O'Connell et al.

(10) Patent No.: US 9,676,872 B2
(45) Date of Patent: Jun. 13, 2017

(54) AFFINITY TAG SYSTEM

(71) Applicant: University College Dublin, Dublin (IE)

(72) Inventors: David O'Connell, Dublin (IE); Sara Linse, Snogerup (SE); Eva Thulin, Bara (SE); Alejandro Merino, Dublin (IE)

(73) Assignee: Northwestern University, Evanston, IL (US)

(*) Notice: Subject to any disclaimer, the term of this patent is extended or adjusted under 35 U.S.C. 154(b) by 0 days.

(21) Appl. No.: 14/369,331

(22) PCT Filed: Jan. 7, 2013

(86) PCT No.: PCT/EP2013/050169
§ 371 (c)(1),
(2) Date: Jun. 27, 2014

(87) PCT Pub. No.: WO2013/102684
PCT Pub. Date: Jul. 11, 2013

(65) Prior Publication Data
US 2015/0005480 A1    Jan. 1, 2015

(30) Foreign Application Priority Data
Jan. 6, 2012  (EP) .................................. 12150412

(51) Int. Cl.
*C07K 17/06*  (2006.01)
*C07K 1/22*   (2006.01)
*C07K 14/47*  (2006.01)

(52) U.S. Cl.
CPC ................ *C07K 17/06* (2013.01); *C07K 1/22* (2013.01); *C07K 14/4728* (2013.01); *C07K 2319/00* (2013.01); *C07K 2319/50* (2013.01)

(58) Field of Classification Search
CPC ... C07K 14/4728; C07K 1/22; C07K 2319/70
See application file for complete search history.

(56) References Cited

U.S. PATENT DOCUMENTS

2010/0297734 A1* 11/2010 McCluskey .............. C07K 1/20
                                                        435/243

FOREIGN PATENT DOCUMENTS

WO      2009046520        4/2009

OTHER PUBLICATIONS

Chen et al. "Fluorescence complementation via EF-hand interactions," Journal of Biotechnology, 142 (2009) 205-213.*

(Continued)

*Primary Examiner* — Christina Bradley
(74) *Attorney, Agent, or Firm* — Andrus Intellectual Property Law, LLP

(57) ABSTRACT

The present invention pertains to an affinity tag system for the immobilization and/or purification of molecules such as biological or organic molecules. The invention provides EF-hand subdomains of calcium binding proteins, such as calbindin D9k, as affinity tags and affinity ligands for immobilizing, detecting and/or for purifying molecules, particularly proteins. Also provided are methods utilizing the affinity tag system of the invention, affinity matrices comprising EF-hand subdomain affinity ligands and fusion proteins comprising EF-hand subdomain affinity tags.

17 Claims, 7 Drawing Sheets

(56) References Cited

OTHER PUBLICATIONS

Lindman et al. "Green fluorescence induced by EF-hand assembly in a split GFP system" Protein Science 2009, vol. 18:1221-1229.*

Vaillancourt et al. "Affinity Purification of Recombinant Proteins Fused to Calmodulin or to Calmodulin-Binding Peptides," Methods in Enzymology, 2000, vol. 326, 340-362.*

Lewit-Bentley et al. "EF-hand calcium binding proteins," Current Opinion in Structural Biology, 2000, 10, 637-643.*

Berggård et al. ("Fragment Complementation Studies of Protein Stabilization by Hydrophobic Core Residues," Biochemistry, 2001, 40, 1257-1264).*

Dell'Orco et al. ("Electrostatic Contributions to the Kinetics and Thermodynamics of Protein Assembly," Biophysical Journal, 2005, 88(3) 1991-2002).*

Berggård et al. ("Fragment complementation of calbindin D28k," Protein Science, 2000, 9, 2094-2108).*

Shuman et al. ("Reconstitution of Calmodulin from Domains and Subdomains: Influence of Target Peptide," J. Mol. Biol., 2006, 358, 870-881).*

Mohapatra et al. "Design of Superparamagnetic Iron Oxide Nanoparticle for Purification of Histidine-Tagged Recombinant Proteins," NSTI-Nanotech, 2007, 2, 291-294.*

Arnau et al., "Current startegies for the use of affinity tags and tag removal for the purification of recombinant proteins", Protein Expression and Purification, Jul. 2006, 48(1):1-13.

Egorov et al., "Purification of a recombinant membrane protein tagged with a calmodulin-binding domain: properties of chimeras of the *Escherichia coli* nicotinamide nucleotide transhydrogenase and the C-terminus of human plasma membrane $Ca^{2+}$-ATPase", Protein Expression and Purification, Jul. 1, 2004, 36(1):31-39.

Linse et al., "Disulfide bonds in homo- and heterodimers of EF-hand subdomains of calbindin D 9k: Stability, calcium binding, and NMR studies", Protein Science, Jun. 1, 1993, 2(6):985-1000.

Yifeng, "Commonly used tag combinations for tandem affinity purification", Biotechnology and Applied Biochemistry, Feb. 2010, 55(2):73-83.

International Search Report for PCT/EP2013/050169 dated Apr. 15, 2013.

Written Opinion for PCT/EP2013/050169 dated Apr. 15, 2013.

David J. O'Connell, et al., "Molecular & Cellular Proteomics 9.6", The American Society for Biochemistry and Molecular Biology, Inc., pp. 1118-1132, 2010.

\* cited by examiner

SEQUENCE LISTING

```
<160> NUMBER OF SEQ ID NOS: 32

<210> SEQ ID NO 1
<211> LENGTH: 32
<212> TYPE: PRT
<213> ORGANISM: Artificial
<220> FEATURE:
<223> OTHER INFORMATION: Fragment

<400> SEQUENCE: 1

Ser Thr Leu Asp Glu Leu Phe Glu Glu Leu Asp Lys Asn Gly Asp Gly
1               5                   10                  15

Glu Val Ser Phe Glu Glu Phe Gln Val Leu Val Lys Lys Ile Ser Gln
            20                  25                  30

<210> SEQ ID NO 2
<211> LENGTH: 43
<212> TYPE: PRT
<213> ORGANISM: Artificial
<220> FEATURE:
<223> OTHER INFORMATION: Fragment

<400> SEQUENCE: 2

Lys Ser Pro Glu Glu Leu Lys Gly Ile Phe Glu Lys Tyr Ala Ala Lys
1               5                   10                  15

Glu Gly Asp Pro Asn Gln Leu Ser Lys Glu Glu Leu Lys Leu Leu Leu
            20                  25                  30

Gly Thr Glu Phe Pro Ser Leu Leu Lys Gly Met
            35                  40

<210> SEQ ID NO 3
<211> LENGTH: 149
<212> TYPE: PRT
<213> ORGANISM: Homo sapiens

<400> SEQUENCE: 3

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Gly Thr Val Met Arg Ser Leu Gly Gln Asn Pro Thr Glu Ala Glu
            35                  40                  45

Leu Gln Asp Met Ile Asn Glu Val Asp Ala Asp Gly Asn Gly Thr Ile
        50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
            115                 120                 125
```

```
Ala Asp Ile Asp Gly Asp Gly Gln Val Asn Tyr Glu Glu Phe Val Gln
            130                 135                 140

Met Met Thr Ala Lys
145

<210> SEQ ID NO 4
<211> LENGTH: 149
<212> TYPE: PRT
<213> ORGANISM: Homo sapiens

<400> SEQUENCE: 4

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
                20                  25                  30

Leu Gly Thr Val Met Arg Ser Leu Gly Gln Asn Pro Thr Glu Ala Glu
            35                  40                  45

Leu Gln Asp Met Ile Asn Glu Val Asp Ala Asp Gly Asn Gly Thr Ile
        50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys
145

<210> SEQ ID NO 5
<211> LENGTH: 148
<212> TYPE: PRT
<213> ORGANISM: Homo sapiens

<400> SEQUENCE: 5

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
                20                  25                  30

Gly Thr Val Met Arg Ser Leu Gly Gln Asn Pro Thr Glu Ala Glu Leu
            35                  40                  45

Gln Asp Met Ile Asn Glu Val Asp Ala Asp Gly Asn Gly Thr Ile Asp
        50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140
```

Met Thr Ala Lys
145

<210> SEQ ID NO 6
<211> LENGTH: 148
<212> TYPE: PRT
<213> ORGANISM: Homo sapiens

<400> SEQUENCE: 6

Ala Asp Gln Leu Thr Glu Glu Gln Val Thr Glu Phe Lys Glu Ala Phe
1               5                   10                  15

Ser Leu Phe Asp Lys Asp Gly Asp Gly Cys Ile Thr Thr Arg Glu Leu
            20                  25                  30

Gly Thr Val Met Arg Ser Leu Gly Gln Asn Pro Thr Glu Ala Glu Leu
        35                  40                  45

Arg Asp Met Met Ser Glu Ile Asp Arg Asp Gly Asn Gly Thr Val Asp
    50                  55                  60

Phe Pro Glu Phe Leu Gly Met Met Ala Arg Lys Met Lys Asp Thr Asp
65                  70                  75                  80

Asn Glu Glu Glu Ile Arg Glu Ala Phe Arg Val Phe Asp Lys Asp Gly
                85                  90                  95

Asn Gly Phe Val Ser Ala Ala Glu Leu Arg His Val Met Thr Arg Leu
            100                 105                 110

Gly Glu Lys Leu Ser Asp Glu Val Asp Glu Met Ile Arg Ala Ala
        115                 120                 125

Asp Thr Asp Gly Asp Gly Gln Val Asn Tyr Glu Glu Phe Val Arg Val
    130                 135                 140

Leu Val Ser Lys
145

<210> SEQ ID NO 7
<211> LENGTH: 146
<212> TYPE: PRT
<213> ORGANISM: Homo sapiens

<400> SEQUENCE: 7

Met Ala Gly Glu Leu Thr Pro Glu Glu Ala Gln Tyr Lys Lys Ala
1               5                   10                  15

Phe Ser Ala Val Asp Thr Asp Gly Asn Gly Thr Ile Asn Ala Gln Glu
            20                  25                  30

Leu Gly Ala Ala Leu Lys Ala Thr Gly Lys Asn Leu Ser Glu Ala Gln
        35                  40                  45

Leu Arg Lys Leu Ile Ser Glu Val Asp Ser Asp Gly Asp Gly Glu Ile
    50                  55                  60

Ser Phe Gln Glu Phe Leu Thr Ala Ala Arg Lys Ala Arg Ala Gly Leu
65                  70                  75                  80

Glu Asp Leu Gln Val Ala Phe Arg Ala Phe Asp Gln Asp Gly Asp Gly
                85                  90                  95

His Ile Thr Val Asp Glu Leu Arg Arg Ala Met Ala Gly Leu Gly Gln
            100                 105                 110

Pro Leu Pro Gln Glu Glu Leu Asp Ala Met Ile Arg Glu Ala Asp Val
        115                 120                 125

Asp Gln Asp Gly Arg Val Asn Tyr Glu Glu Phe Ala Arg Met Leu Ala
    130                 135                 140

Gln Glu
145

```
<210> SEQ ID NO 8
<211> LENGTH: 181
<212> TYPE: PRT
<213> ORGANISM: Homo sapiens

<400> SEQUENCE: 8

Met Gly Leu Gln Gln Glu Ile Ser Leu Gln Pro Trp Cys His His Pro
 1               5                  10                  15

Ala Glu Ser Cys Gln Thr Thr Thr Asp Met Thr Glu Arg Leu Ser Ala
                20                  25                  30

Glu Gln Ile Lys Glu Tyr Lys Gly Val Phe Glu Met Phe Asp Glu Glu
            35                  40                  45

Gly Asn Gly Glu Val Lys Thr Gly Glu Leu Glu Trp Leu Met Ser Leu
        50                  55                  60

Leu Gly Ile Asn Pro Thr Lys Ser Glu Leu Ala Ser Met Ala Lys Asp
 65                  70                  75                  80

Val Asp Arg Asp Asn Lys Gly Phe Phe Asn Cys Asp Gly Phe Leu Ala
                85                  90                  95

Leu Met Gly Val Tyr His Glu Lys Ala Gln Asn Gln Glu Ser Glu Leu
            100                 105                 110

Arg Ala Ala Phe Arg Val Phe Asp Lys Glu Gly Lys Gly Tyr Ile Asp
        115                 120                 125

Trp Asn Thr Leu Lys Tyr Val Leu Met Asn Ala Gly Glu Pro Leu Asn
130                 135                 140

Glu Val Glu Ala Glu Gln Met Met Lys Glu Ala Asp Lys Asp Gly Asp
145                 150                 155                 160

Arg Thr Ile Asp Tyr Glu Glu Phe Val Ala Met Met Thr Gly Glu Ser
                165                 170                 175

Phe Lys Leu Ile Gln
            180

<210> SEQ ID NO 9
<211> LENGTH: 260
<212> TYPE: PRT
<213> ORGANISM: Homo sapiens

<400> SEQUENCE: 9

Ala Glu Ser His Leu Gln Ser Ser Leu Ile Thr Ala Ser Gln Phe Phe
 1               5                  10                  15

Glu Ile Trp Leu His Phe Asp Ala Asp Gly Ser Gly Tyr Leu Glu Gly
                20                  25                  30

Lys Glu Leu Gln Asn Leu Ile Gln Glu Leu Gln Gln Ala Arg Lys Lys
            35                  40                  45

Ala Gly Leu Glu Leu Ser Pro Glu Met Lys Thr Phe Val Asp Gln Tyr
        50                  55                  60

Gly Gln Arg Asp Asp Gly Lys Ile Gly Ile Val Glu Leu Ala His Val
 65                  70                  75                  80

Leu Pro Thr Glu Glu Asn Phe Leu Leu Leu Phe Arg Cys Gln Gln Leu
                85                  90                  95

Lys Ser Cys Glu Glu Phe Met Lys Thr Trp Arg Lys Tyr Asp Thr Asp
            100                 105                 110

His Ser Gly Phe Ile Glu Thr Glu Glu Leu Lys Asn Phe Leu Lys Asp
        115                 120                 125

Leu Leu Glu Lys Ala Asn Lys Thr Val Asp Asp Thr Lys Leu Ala Glu
130                 135                 140
```

```
Tyr Thr Asp Leu Met Leu Lys Leu Phe Asp Ser Asn Asn Asp Gly Lys
145                 150                 155                 160

Leu Glu Leu Thr Glu Met Ala Arg Leu Leu Pro Val Gln Glu Asn Phe
                165                 170                 175

Leu Leu Lys Phe Gln Gly Ile Lys Met Cys Gly Lys Glu Phe Asn Lys
            180                 185                 190

Ala Phe Glu Leu Tyr Asp Gln Asp Gly Asn Gly Tyr Ile Asp Glu Asn
                195                 200                 205

Glu Leu Asp Ala Leu Leu Lys Asp Leu Cys Glu Lys Asn Lys Gln Asp
210                 215                 220

Leu Asp Ile Asn Asn Ile Thr Thr Tyr Lys Lys Asn Ile Met Ala Leu
225                 230                 235                 240

Ser Asp Gly Gly Lys Leu Tyr Arg Thr Asp Leu Ala Leu Ile Leu Cys
                245                 250                 255

Ala Gly Asp Asn
            260

<210> SEQ ID NO 10
<211> LENGTH: 271
<212> TYPE: PRT
<213> ORGANISM: Homo sapiens

<400> SEQUENCE: 10

Met Ala Gly Pro Gln Gln Pro Pro Tyr Leu His Leu Ala Glu Leu
1               5                   10                  15

Thr Ala Ser Gln Phe Leu Glu Ile Trp Lys His Phe Asp Ala Asp Gly
                20                  25                  30

Asn Gly Tyr Ile Glu Gly Lys Glu Leu Glu Asn Phe Phe Gln Glu Leu
            35                  40                  45

Glu Lys Ala Arg Lys Gly Ser Gly Met Met Ser Lys Ser Asp Asn Phe
50                  55                  60

Gly Glu Lys Met Lys Glu Phe Met Gln Lys Tyr Asp Lys Asn Ser Asp
65                  70                  75                  80

Gly Lys Ile Glu Met Ala Glu Leu Ala Gln Ile Leu Pro Thr Glu Glu
                85                  90                  95

Asn Phe Leu Leu Cys Phe Arg Gln His Val Gly Ser Ser Ala Glu Phe
            100                 105                 110

Met Glu Ala Trp Arg Lys Tyr Asp Thr Asp Arg Ser Gly Tyr Ile Glu
            115                 120                 125

Ala Asn Glu Leu Lys Gly Phe Leu Ser Asp Leu Leu Lys Lys Ala Asn
130                 135                 140

Arg Pro Tyr Asp Glu Pro Lys Leu Gln Glu Tyr Thr Gln Thr Ile Leu
145                 150                 155                 160

Arg Met Phe Asp Leu Asn Gly Asp Gly Lys Leu Gly Leu Ser Glu Met
                165                 170                 175

Ser Arg Leu Leu Pro Val Gln Glu Asn Phe Leu Leu Lys Phe Gln Gly
            180                 185                 190

Met Lys Leu Thr Ser Glu Glu Phe Asn Ala Ile Phe Thr Phe Tyr Asp
            195                 200                 205

Lys Asp Arg Ser Gly Tyr Ile Asp Glu His Glu Leu Asp Ala Leu Leu
210                 215                 220

Lys Asp Leu Tyr Glu Lys Asn Lys Lys Glu Met Asn Ile Gln Gln Leu
225                 230                 235                 240

Thr Asn Tyr Arg Lys Ser Val Met Ser Leu Ala Glu Ala Gly Lys Leu
```

```
                    245                 250                 255
Tyr Arg Lys Asp Leu Glu Ile Val Leu Cys Ser Glu Pro Pro Met
            260                 265                 270
```

<210> SEQ ID NO 11
<211> LENGTH: 79
<212> TYPE: PRT
<213> ORGANISM: Homo sapiens

<400> SEQUENCE: 11

```
Met Ser Thr Lys Lys Ser Pro Glu Glu Leu Lys Arg Ile Phe Glu Lys
1               5                   10                  15
Tyr Ala Ala Lys Glu Gly Asp Pro Asp Gln Leu Ser Lys Asp Glu Leu
                20                  25                  30
Lys Leu Leu Ile Gln Ala Glu Phe Pro Ser Leu Leu Lys Gly Pro Asn
            35                  40                  45
Thr Leu Asp Asp Leu Phe Gln Glu Leu Asp Lys Asn Gly Asp Gly Glu
        50                  55                  60
Val Ser Phe Glu Glu Phe Gln Val Leu Val Lys Ile Ser Gln
65                  70                  75
```

<210> SEQ ID NO 12
<211> LENGTH: 200
<212> TYPE: PRT
<213> ORGANISM: Homo sapiens

<400> SEQUENCE: 12

```
Met Gly Asn Ser Lys Ser Gly Ala Leu Ser Lys Glu Ile Leu Glu Glu
1               5                   10                  15
Leu Gln Leu Asn Thr Lys Phe Ser Glu Glu Leu Cys Ser Trp Tyr
                20                  25                  30
Gln Ser Phe Leu Lys Asp Cys Pro Thr Gly Arg Ile Thr Gln Gln Gln
            35                  40                  45
Phe Gln Ser Ile Tyr Ala Lys Phe Phe Pro Asp Thr Asp Pro Lys Ala
        50                  55                  60
Tyr Ala Gln His Val Phe Arg Ser Phe Asp Ser Asn Leu Asp Gly Thr
65                  70                  75                  80
Leu Asp Phe Lys Glu Tyr Val Ile Ala Leu His Met Thr Thr Ala Gly
                85                  90                  95
Lys Thr Asn Gln Lys Leu Glu Trp Ala Phe Ser Leu Tyr Asp Val Asp
            100                 105                 110
Gly Asn Gly Thr Ile Ser Lys Asn Glu Val Leu Glu Ile Val Met Ala
        115                 120                 125
Ile Phe Lys Met Ile Thr Pro Glu Asp Val Lys Leu Leu Pro Asp Asp
130                 135                 140
Glu Asn Thr Pro Glu Lys Arg Ala Glu Lys Ile Trp Lys Tyr Phe Gly
145                 150                 155                 160
Lys Asn Asp Asp Asp Lys Leu Thr Glu Lys Glu Phe Ile Glu Gly Thr
                165                 170                 175
Leu Ala Asn Lys Glu Ile Leu Arg Leu Ile Gln Phe Glu Pro Gln Lys
            180                 185                 190
Val Lys Glu Lys Met Lys Asn Ala
        195                 200
```

<210> SEQ ID NO 13
<211> LENGTH: 190
<212> TYPE: PRT

<213> ORGANISM: Homo sapiens

<400> SEQUENCE: 13

Met Gly Lys Ser Asn Ser Lys Leu Lys Pro Glu Val Val Glu Glu Leu
1               5                   10                  15

Thr Arg Lys Thr Tyr Phe Thr Glu Lys Glu Val Gln Gln Trp Tyr Lys
                20                  25                  30

Gly Phe Ile Lys Asp Cys Pro Ser Gly Gln Leu Asp Ala Ala Gly Phe
            35                  40                  45

Gln Lys Ile Tyr Lys Gln Phe Phe Pro Phe Gly Asp Pro Thr Lys Phe
        50                  55                  60

Ala Thr Phe Val Phe Asn Val Phe Asp Glu Asn Lys Asp Gly Arg Ile
65                  70                  75                  80

Glu Phe Ser Glu Phe Ile Gln Ala Leu Ser Val Thr Ser Arg Gly Thr
                85                  90                  95

Leu Asp Glu Lys Leu Arg Trp Ala Phe Lys Leu Tyr Asp Leu Asp Asn
                100                 105                 110

Asp Gly Tyr Ile Thr Arg Asn Glu Met Leu Asp Ile Val Asp Ala Ile
            115                 120                 125

Tyr Gln Met Val Gly Asn Thr Val Glu Leu Pro Glu Glu Asn Thr
        130                 135                 140

Pro Glu Lys Arg Val Asp Arg Ile Phe Ala Met Met Asp Lys Asn Ala
145                 150                 155                 160

Asp Gly Lys Leu Thr Leu Gln Glu Phe Gln Glu Gly Ser Lys Ala Asp
                165                 170                 175

Pro Ser Ile Val Gln Ala Leu Ser Leu Tyr Asp Gly Leu Val
            180                 185                 190

<210> SEQ ID NO 14
<211> LENGTH: 161
<212> TYPE: PRT
<213> ORGANISM: Homo sapiens

<400> SEQUENCE: 14

Met Asp Asp Ile Tyr Lys Ala Ala Val Glu Gln Leu Thr Glu Glu Gln
1               5                   10                  15

Lys Asn Glu Phe Lys Ala Ala Phe Asp Ile Phe Val Leu Gly Ala Glu
                20                  25                  30

Asp Gly Cys Ile Ser Thr Lys Glu Leu Gly Lys Val Met Arg Met Leu
            35                  40                  45

Gly Gln Asn Pro Thr Pro Glu Glu Leu Gln Glu Met Ile Asp Glu Val
        50                  55                  60

Asp Glu Asp Gly Ser Gly Thr Val Asp Phe Asp Glu Phe Leu Val Met
65                  70                  75                  80

Met Val Arg Cys Met Lys Asp Asp Ser Lys Gly Lys Ser Glu Glu Glu
                85                  90                  95

Leu Ser Asp Leu Phe Arg Met Phe Asp Lys Asn Ala Asp Gly Tyr Ile
                100                 105                 110

Asp Leu Asp Glu Leu Lys Ile Met Leu Gln Ala Thr Gly Glu Thr Ile
            115                 120                 125

Thr Glu Asp Asp Ile Glu Glu Leu Met Lys Asp Gly Asp Lys Asn Asn
        130                 135                 140

Asp Gly Arg Ile Asp Tyr Asp Glu Phe Leu Glu Phe Met Lys Gly Val
145                 150                 155                 160

Glu

<210> SEQ ID NO 15
<211> LENGTH: 110
<212> TYPE: PRT
<213> ORGANISM: Homo sapiens

<400> SEQUENCE: 15

Met Ser Met Thr Asp Leu Leu Asn Ala Glu Asp Ile Lys Lys Ala Val
1               5                   10                  15

Gly Ala Phe Ser Ala Thr Asp Ser Phe Asp His Lys Lys Phe Phe Gln
            20                  25                  30

Met Val Gly Leu Lys Lys Lys Ser Ala Asp Val Lys Lys Val Phe
        35                  40                  45

His Met Leu Asp Lys Asp Lys Ser Gly Phe Ile Glu Glu Asp Glu Leu
    50                  55                  60

Gly Phe Ile Leu Lys Gly Phe Ser Pro Asp Ala Arg Asp Leu Ser Ala
65                  70                  75                  80

Lys Glu Thr Lys Met Leu Met Ala Ala Gly Asp Lys Asp Gly Asp Gly
                85                  90                  95

Lys Ile Gly Val Asp Glu Phe Ser Thr Leu Val Ala Glu Ser
            100                 105                 110

<210> SEQ ID NO 16
<211> LENGTH: 261
<212> TYPE: PRT
<213> ORGANISM: Homo sapiens

<400> SEQUENCE: 16

Met Ala Glu Ser His Leu Gln Ser Ser Leu Ile Thr Ala Ser Gln Phe
1               5                   10                  15

Phe Glu Ile Trp Leu His Phe Asp Ala Asp Gly Ser Gly Tyr Leu Glu
            20                  25                  30

Gly Lys Glu Leu Gln Asn Leu Ile Gln Glu Leu Gln Gln Ala Arg Lys
        35                  40                  45

Lys Ala Gly Leu Glu Leu Ser Pro Glu Met Lys Thr Phe Val Asp Gln
    50                  55                  60

Tyr Gly Gln Arg Asp Asp Gly Lys Ile Gly Ile Val Glu Leu Ala His
65                  70                  75                  80

Val Leu Pro Thr Glu Glu Asn Phe Leu Leu Leu Phe Arg Cys Gln Gln
                85                  90                  95

Leu Lys Ser Cys Glu Glu Phe Met Lys Thr Trp Arg Lys Tyr Asp Thr
            100                 105                 110

Asp His Ser Gly Phe Ile Glu Thr Glu Glu Leu Lys Asn Phe Leu Lys
        115                 120                 125

Asp Leu Leu Glu Lys Ala Asn Lys Thr Val Asp Asp Thr Lys Leu Ala
    130                 135                 140

Glu Tyr Thr Asp Leu Met Leu Lys Leu Phe Asp Ser Asn Asn Asp Gly
145                 150                 155                 160

Lys Leu Glu Leu Thr Glu Met Ala Arg Leu Leu Pro Val Gln Glu Asn
                165                 170                 175

Phe Leu Leu Lys Phe Gln Gly Ile Lys Met Cys Gly Lys Glu Phe Asn
            180                 185                 190

Lys Ala Phe Glu Leu Tyr Asp Gln Asp Gly Asn Gly Tyr Ile Asp Glu
        195                 200                 205

Asn Glu Leu Asp Ala Leu Leu Lys Asp Leu Cys Glu Lys Asn Lys Gln
    210                 215                 220

```
Asp Leu Asp Ile Asn Asn Ile Thr Thr Tyr Lys Lys Asn Ile Met Ala
225                 230                 235                 240

Leu Ser Asp Gly Gly Lys Leu Tyr Arg Thr Asp Leu Ala Leu Ile Leu
            245                 250                 255

Cys Ala Gly Asp Asn
            260

<210> SEQ ID NO 17
<211> LENGTH: 276
<212> TYPE: PRT
<213> ORGANISM: Homo sapiens

<400> SEQUENCE: 17

Met Asp Ser Ser Arg Glu Pro Thr Leu Gly Arg Leu Asp Ala Ala Gly
1               5                   10                  15

Phe Trp Gln Val Trp Gln Arg Phe Asp Ala Asp Glu Lys Gly Tyr Ile
                20                  25                  30

Glu Glu Lys Glu Leu Asp Ala Phe Phe Leu His Met Leu Met Lys Leu
            35                  40                  45

Gly Thr Asp Asp Thr Val Met Lys Ala Asn Leu His Lys Val Lys Gln
        50                  55                  60

Gln Phe Met Thr Thr Gln Asp Ala Ser Lys Asp Gly Arg Ile Arg Met
65                  70                  75                  80

Lys Glu Leu Ala Gly Met Phe Leu Ser Glu Asp Glu Asn Phe Leu Leu
                85                  90                  95

Leu Phe Arg Arg Glu Asn Pro Leu Asp Ser Ser Val Glu Phe Met Gln
                100                 105                 110

Ile Trp Arg Lys Tyr Asp Ala Asp Ser Ser Gly Phe Ile Ser Ala Ala
            115                 120                 125

Glu Leu Arg Asn Phe Leu Arg Asp Leu Phe Leu His His Lys Lys Ala
        130                 135                 140

Ile Ser Glu Ala Lys Leu Glu Glu Tyr Thr Gly Thr Met Met Lys Ile
145                 150                 155                 160

Phe Asp Arg Asn Lys Asp Gly Arg Leu Asp Leu Asn Asp Leu Ala Arg
                165                 170                 175

Ile Leu Ala Leu Gln Glu Asn Phe Leu Leu Gln Phe Lys Met Asp Ala
                180                 185                 190

Cys Ser Thr Glu Glu Arg Lys Arg Asp Phe Glu Lys Ile Phe Ala Tyr
            195                 200                 205

Tyr Asp Val Ser Lys Thr Gly Ala Leu Glu Gly Pro Glu Val Asp Gly
        210                 215                 220

Phe Val Lys Asp Met Met Glu Leu Val Gln Pro Ser Ile Ser Gly Val
225                 230                 235                 240

Asp Leu Asp Lys Phe Arg Glu Ile Leu Leu Arg His Cys Asp Val Asn
                245                 250                 255

Lys Asp Gly Lys Ile Gln Lys Ser Glu Leu Ala Leu Cys Leu Gly Leu
                260                 265                 270

Lys Ile Asn Pro
        275

<210> SEQ ID NO 18
<211> LENGTH: 271
<212> TYPE: PRT
<213> ORGANISM: Homo sapiens

<400> SEQUENCE: 18
```

Met Ala Gly Pro Gln Gln Pro Pro Tyr Leu His Leu Ala Glu Leu
1               5                   10                  15

Thr Ala Ser Gln Phe Leu Glu Ile Trp Lys His Phe Asp Ala Asp Gly
            20                  25                  30

Asn Gly Tyr Ile Glu Gly Lys Glu Leu Glu Asn Phe Phe Gln Glu Leu
            35                  40                  45

Glu Lys Ala Arg Lys Gly Ser Gly Met Met Ser Lys Ser Asp Asn Phe
50                  55                  60

Gly Glu Lys Met Lys Glu Phe Met Gln Lys Tyr Asp Lys Asn Ser Asp
65                  70                  75                  80

Gly Lys Ile Glu Met Ala Glu Leu Ala Gln Ile Leu Pro Thr Glu Glu
                85                  90                  95

Asn Phe Leu Leu Cys Phe Arg Gln His Val Gly Ser Ser Ala Glu Phe
            100                 105                 110

Met Glu Ala Trp Arg Lys Tyr Asp Thr Asp Arg Ser Gly Tyr Ile Glu
            115                 120                 125

Ala Asn Glu Leu Lys Gly Phe Leu Ser Asp Leu Leu Lys Lys Ala Asn
130                 135                 140

Arg Pro Tyr Asp Glu Pro Lys Leu Gln Glu Tyr Thr Gln Thr Ile Leu
145                 150                 155                 160

Arg Met Phe Asp Leu Asn Gly Asp Gly Lys Leu Gly Leu Ser Glu Met
                165                 170                 175

Ser Arg Leu Leu Pro Val Gln Glu Asn Phe Leu Leu Lys Phe Gln Gly
            180                 185                 190

Met Lys Leu Thr Ser Glu Glu Phe Asn Ala Ile Phe Thr Phe Tyr Asp
            195                 200                 205

Lys Asp Arg Ser Gly Tyr Ile Asp Glu His Glu Leu Asp Ala Leu Leu
210                 215                 220

Lys Asp Leu Tyr Glu Lys Asn Lys Lys Glu Met Asn Ile Gln Gln Leu
225                 230                 235                 240

Thr Asn Tyr Arg Lys Ser Val Met Ser Leu Ala Glu Ala Gly Lys Leu
                245                 250                 255

Tyr Arg Lys Asp Leu Glu Ile Val Leu Cys Ser Glu Pro Pro Met
            260                 265                 270

```
<210> SEQ ID NO 19
<211> LENGTH: 4185
<212> TYPE: DNA
<213> ORGANISM: Artificial
<220> FEATURE:
<223> OTHER INFORMATION: Plasmid

<400> SEQUENCE: 19
```

| | | | | |
|---|---|---|---|---|
| ctcatgacca aaatccctta acgtgagtta cgcgcgcgtc gttccactga gcgtcagacc | 60 |
| ccgtagaaaa gatcaaagga tcttcttgag atcctttttt tctgcgcgta atctgctgct | 120 |
| tgcaaacaaa aaaaccaccg ctaccagcgg tggtttgttt gccggatcaa gagctaccaa | 180 |
| ctcttttttcc gaaggtaact ggcttcagca gagcgcagat accaaatact gttcttctag | 240 |
| tgtagccgta gttagcccac cacttcaaga actctgtagc accgcctaca tacctcgctc | 300 |
| tgctaatcct gttaccagtg ctgctgccag tggcgataag tcgtgtctt accgggttgg | 360 |
| actcaagacg atagttaccg gataaggcgc agcggtcggg ctgaacgggg ggttcgtgca | 420 |
| cacagcccag cttggagcga acgacctaca ccgaactgag atacctacag cgtgagctat | 480 |
| gagaaagcgc cacgcttccc gaagggagaa aggcggacag gtatccggta agcggcaggg | 540 |

```
tcggaacagg agagcgcacg agggagcttc caggggggaaa cgcctggtat ctttatagtc    600
ctgtcgggtt tcgccacctc tgacttgagc gtcgattttt gtgatgctcg tcagggggggc    660 ggagcctatg gaaaaacgcc agcaacgcgg ccttttttacg gttcctggcc ttttgctggc    720
cttttgctca catgttcttt cctgcgttat cccctgattc tgtggataac cgtattaccg    780
cctttgagtg agctgatacc gctcgccgca gccgaacgac cgagcgcagc gagtcagtga    840
gcgaggaagc ggaaggcgag agtagggaac tgccaggcat caaactaagc agaaggcccc    900
tgacggatgg cctttttgcg tttctacaaa ctctttctgt gttgtaaaac gacggccagt    960
cttaagctcg ggcccccttgg gcggttctga taacgagtaa tcgttaatcc gcaaataacg    1020
taaaaacccg cttcggcggg ttttttttatg gggggagttt agggaaagag catttgtcag    1080
aatatttaag ggcgcctgtc actttgcttg atatatgaga attatttaac cttataaatg    1140
agaaaaaagc aacgcacttt aaataagata cgttgctttt tcgattgatg aacacctata    1200
attaaactat tcatctatta tttatgattt tttgtatata caatatttct agtttgttaa    1260
agagaattaa gaaaataaat ctcgaaaata ataagggaa aatcagtttt tgatatcaaa    1320
attatacatg tcaacgataa tacaaaatat aatacaaact ataagatgtt atcagtattt    1380
attatgcatt tagaataaat tttgtgtcgc ccttccgcga aattaatacg actcactata    1440
ggggaattgt gagcggataa caattcccct ctagaaataa ttttgtttaa cttttaggag    1500
ataaaacata tgaaatacct attgcctacg gcagccgctg gattgttatt actcgcggcc    1560
cagccggcca tggccgagat gacccaggcg gccgcaggcg gttctggttc cggtagcagc    1620
aagagcccgg aagagctgaa aggcatcttc gagaagtatg cggcgaaaga gggcgacccg    1680
aaccaactga gcaaagaaga actgaagctg ctgctgcaaa ccgagtttcc gagcctgctg    1740
aagggtatgt aactcgagcc ccctagcata acccccttggg gcctctaaac gggtcttgag    1800
gggttttttg cccctgagac gcgtcaatcg agttcgtacc taagggcgac accccctaat    1860
tagcccgggc gaaaggccca gtcttcgac tgagccttc gtttattg atgcctggca    1920 gttccctact ctcgcatggg gagtccccac actaccatcg gcgctacggc gtttcacttc    1980
tgagttcggc atggggtcag gtgggaccac cgcgctactc cgccaggca acaagggggt    2040 gttatgagcc atattcaggt ataaatgggc tcgcgataat gttcagaatt ggttaattgg    2100
ttgtaacact gaccccctatt tgtttatttt tctaaataca ttcaaatatg tatccgctca    2160
tgagacaata accctgataa atgcttcaat aatattgaaa aaggaagaat atgagccata    2220
ttcaacggga aacgtcgagg ccgcgattaa attccaacat ggatgctgat ttatatgggt    2280
ataaatgggc tcgcgataat gtcgggcaat caggtgcgac aatctatcgc ttgtatggga    2340
agcccgatgc gccagagttg tttctgaaac atggcaaagg tagcgttgcc aatgatgtta    2400
cagatgagat ggtcagacta aactggctga cggaatttat gccacttccg accatcaagc    2460
attttatccg tactcctgat gatgcatggt tactcaccac tgcgatcccc ggaaaaacag    2520
cgttccaggt attagaagaa tatcctgatt caggtgaaaa tattgttgat gcgctggcag    2580
tgttcctgcg ccggttgcac tcgattcctg tttgtaattg tccttttaac agcgatcgcg    2640
tatttcgcct cgctcaggcg caatcacgaa tgaataacgg tttggttgat gcgagtgatt    2700
ttgatgacga gcgtaatggc tggcctgttg aacaagtctg gaaagaaatg cataaacttt    2760
tgccattctc accggattca gtcgtcactc atggtgattt ctcacttgat aaccttattt    2820
ttgacgaggg gaaattaata ggttgtattg atgttggacg agtcggaatc gcagaccgat    2880
```

```
accaggatct tgccatccta tggaactgcc tcggtgagtt ttctccttca ttacagaaac    2940 ggcttttttca aaaatatggt attgataatc ctgatatgaa taaattgcag tttcatttga    3000
tgctcgatga gtttttctaa gcggcgcgcc atcgaatggc gcaaaaccctt tcgcggtatg   3060 gcatgatagc gcccggaaga gagtcaattc agggtggtga atatgaaacc agtaacgtta    3120
tacgatgtcg cagagtatgc cggtgtctct tatcagaccg tttcccgcgt ggtgaaccag    3180
gccagccacg tttctgcgaa aacgcgggaa aaagtggaag cggcgatggc ggagctgaat    3240
tacattccca accgcgtggc acaacaactg gcgggcaaac agtcgttgct gattggcgtt    3300
gccacctcca gtctggccct gcacgcgccg tcgcaaattg tcgcggcgat taaatctcgc    3360
gccgatcaac tgggtgccag cgtggtggtg tcgatggtag aacgaagcgg cgtcgaagcc    3420
tgtaaagcgg cggtgcacaa tcttctcgcg caacgcgtca gtgggctgat cattaactat    3480
ccgctggatg accaggatgc cattgctgtg gaagctgcct gcactaatgt tccggcgtta    3540
tttcttgatg tctctgacca gacacccatc aacagtatta ttttctccca tgaggacggt    3600
acgcgactgg gcgtggagca tctggtcgca ttgggtcacc agcaaatcgc gctgttagcg    3660
ggcccattaa gttctgtctc ggcgcgtctg cgtctggctg gctggcataa atatctcact    3720
cgcaatcaaa ttcagccgat agcggaacgg gaaggcgact ggagtgccat gtccggtttt    3780
caacaaacca tgcaaatgct gaatgagggc atcgttccca ctgcgatgct ggttgccaac    3840
gatcagatgg cgctgggcgc aatgcgcgcc attaccgagt ccgggctgcg cgttggtgcg    3900
gatatctcgg tagtgggata cgacgatacc gaagatagct catgttatat cccgccgtta    3960
accaccatca acaggattt tcgcctgctg gggcaaacca gcgtggaccg cttgctgcaa    4020
ctctctcagg gccaggcggt gaagggcaat cagctgttgc cagtctcact ggtgaaaaga    4080
aaaaccaccc tggcgcccaa tacgcaaacc gcctctcccc gcgcgttggc cgattcatta    4140
atgcagctgg cacgacaggt ttcccgactg gaaagcgggc agtga                    4185
```

<210> SEQ ID NO 20
<211> LENGTH: 4301
<212> TYPE: DNA
<213> ORGANISM: Artificial
<220> FEATURE:
<223> OTHER INFORMATION: Plasmid

<400> SEQUENCE: 20

```
aattgtgagc ggataacaat tacgagcttc atgcacagtg aaatcatgaa aatttatttt     60
gctttgtgag cggataacaa ttataatatg tggaattgtg agcgctcaca attccacaac    120
ggtttccctc tagaaataat tttgtttaac tttaagaag gagatataca tatgcgggt     180 tctcatcacc atcaccatca cggtatggct agcatgactg gtggacagca aatgggtcgg    240
aagtctccag aagaactgaa gggcattttc gaaaaatatg cagccaaaga aggtgatcca    300
aaccaactgt ccaaggagga gctgaagcta ctgcttcaga cggaattccc cagtttgctg    360
aagggtccac gatgggatc cgagctcgag atctgcagct ggtaccatgg tactcgaagc    420
ttgatccggc tgctaacaaa gcccgaaagg aagctgagtt ggctgctgcc accgctgagc    480
aataactagc cccaagggcg acacaaaatt tattctaaat gataataaat actgataaca    540
tcttatagtt tgtattatat tttgtattat cgttgacatg tataattttg atatcaaaaa    600
ctgattttcc ctttattatt ttcgagattt attttcttaa ttctctttaa caaactagaa    660
atattgtata tacaaaaaat cataaatat agatgaatag tttaattata ggtgttcatc    720
aatcgaaaaa gcaacgtatc ttatttaaag tgcgttgctt ttttctcatt tataaggtta    780
```

```
aataattctc atatatcaag caaagtgaca ggcgcccctta aatattctga caaatgctct    840
ttccctaaac tcccccccata aaaaaacccg ccgaagcggg ttttacgtt atttgcggat     900 taacgattac tcgttatcag aaccgcccag ggggcccgag cttaagactg gccgtcgttt    960
tacaacacag aaagagtttg tagaaacgca aaaaggccat ccgtcagggg ccttctgctt   1020
agtttgatgc ctggcagttc cctactctcg ccttccgctt cctcgctcac tgactcgctg   1080
cgctcggtcg ttcggctgcg cgagcggta tcagctcact caaaggcggt aatacggtta    1140
tccacagaat caggggataa cgcaggaaag aacatgtgag caaaaggcca gcaaaaggcc   1200
aggaaccgta aaaaggccgc gttgctggcg ttttccata ggctccgccc ccctgacgag     1260
catcacaaaa atcgacgctc aagtcagagg tggcgaaacc cgacaggact ataaagatac   1320
caggcgtttc ccctggaag ctccctcgtg cgctctcctg ttccgaccct gccgcttacc     1380
ggatacctgt ccgcctttct cccttcggga agcgtggcgc tttctcatag ctcacgctgt   1440
aggtatctca gttcggtgta ggtcgttcgc tccaagctgg gctgtgtgca cgaacccccc   1500
gttcagcccg accgctgcgc cttatccggt aactatcgtc ttgagtccaa cccggtaaga   1560
cacgacttat cgccactggc agcagccact ggtaacagga ttagcagagc gaggtatgta   1620
ggcggtgcta cagagttctt gaagtggtgg gctaactacg gctacactag aagaacagta   1680
tttggtatct gcgctctgct gaagccagtt accttcggaa aaagagttgg tagctcttga   1740
tccggcaaac aaaccaccgc tggtagcggt ggtttttttg tttgcaagca gcagattacg   1800
cgcagaaaaa aaggatctca agaagatcct ttgatctttt ctacgggtc tgacgctcag    1860 tggaacgacg cgcgcgtaac tcacgttaag ggattttggt catgagtcac tgcccgcttt   1920
ccagtcggga aacctgtcgt gccagctgca ttaatgaatc ggccaacgcg cggggagagg   1980
cggtttgcgt attgggcgcc agggtggttt ttcttttcac cagtgagact ggcaacagct   2040 gattgcccctt caccgcctgg ccctgagaga gttgcagcaa gcggtccacg ctggtttgcc   2100
ccagcaggcg aaaatcctgt ttgatggtgg ttaacggcgg gatataacat gagctatctt   2160
cggtatcgtc gtatcccact accgagatat ccgcaccaac gcgcagcccg gactcggtaa   2220
tggcgcgcat tgcgcccagc gccatctgat cgttggcaac cagcatcgca gtgggaacga   2280
tgccctcatt cagcatttgc atggtttgtt gaaaaccgga catggcactc cagtcgcctt   2340
cccgttccgc tatcggctga atttgattgc gagtgagata tttatgccag ccagccagac   2400
gcagacgcgc cgagacagaa cttaatgggc ccgctaacag cgcgatttgc tggtgaccca   2460
atgcgaccag atgctccacg cccagtcgcg taccgtcctc atgggagaaa ataatactgt   2520
tgatgggtgt ctggtcagag acatcaagaa ataacgccgg aacattagtg caggcagctt   2580
ccacagcaat ggcatcctgg tcatccagcg gatagttaat gatcagccca ctgacgcgtt   2640
gcgcgagaag attgtgcacc gccgctttac aggcttcgac gccgcttcgt tctaccatcg   2700
acaccaccac gctggcaccc agttgatcgg cgcgagattt aatcgccgcg acaatttgcg   2760
acggcgcgtg cagggccaga ctggaggtgg caacgccaat cagcaacgac tgtttgcccg   2820
ccagttgttg tgccacgcgg ttgggaatgt aattcagctc cgccatcgcc gcttccactt   2880
tttcccgcgt tttcgcagaa acgtggctgg cctggttcac cacgcgggaa acggtctgat   2940
aagagacacc ggcatactct gcgacatcgt ataacgttac tggtttcata ttcaccaccc   3000
tgaattgact ctcttccggg cgctatcatg ccataccgcg aaaggttttg cgccattcga   3060
tggcgcgccg cttaccaatg cttaatcagt gaggcaccta tctcagcgat ctgtctattt   3120
```

```
cgttcatcca tagttgcctg actccccgtc gtgtagataa ctacgatacg ggagggctta    3180
ccatctggcc ccagcgctgc gatgataccg cgagaaccac gctcaccggc tccggattta    3240
tcagcaataa accagccagc cggaagggcc gagcgcagaa gtggtcctgc aactttatcc    3300
gcctccatcc agtctattaa ttgttgccgg gaagctagag taagtagttc gccagttaat    3360
agtttgcgca acgttgttgc catcgctaca ggcatcgtgg tgtcacgctc gtcgtttggt    3420
atggcttcat tcagctccgg ttcccaacga tcaaggcgag ttacatgatc ccccatgttg    3480
tgcaaaaaag cggttagctc cttcggtcct ccgatcgttg tcagaagtaa gttggccgca    3540
gtgttatcac tcatggttat ggcagcactg cataattctc ttactgtcat gccatccgta    3600
agatgctttt ctgtgactgg tgagtactca accaagtcat tctgagaata gtgtatgcgg    3660
cgaccgagtt gctcttgccc ggcgtcaata cgggataata ccgcgccaca tagcagaact    3720
ttaaaagtgc tcatcattgg aaaacgttct tcggggcgaa aactctcaag gatcttaccg    3780
ctgttgagat ccagttcgat gtaacccact cgtgcaccca actgatcttc agcatctttt    3840
actttcacca gcgtttctgg gtgagcaaaa acaggaaggc aaaatgccgc aaaaaaggga    3900
ataagggcga cacggaaatg ttgaatactc atattcttcc ttttcaata ttattgaagc    3960 atttatcagg gttattgtct catgagcgga tacatatttg aatgtattta gaaaaataaa    4020 caaataggg tcagtgttac aaccaattaa ccaattctga acattatcgc gagcccattt    4080
atacctgaat atggctcata acaccccttg tttgcctggc ggcagtagcg cggtggtccc    4140
acctgacccc atgccgaact cagaagtgaa acgccgtagc gccgatggta gtgtggggac    4200
tccccatgcg agagtaggga actgccaggc atcaaataaa acgaaaggct cagtcgaaag    4260
actgggcctt tcgccggc taattatggg gtgtcgccct t                        4301
```

<210> SEQ ID NO 21
<211> LENGTH: 4236
<212> TYPE: DNA
<213> ORGANISM: Artificial
<220> FEATURE:
<223> OTHER INFORMATION: Plasmid

<400> SEQUENCE: 21

```
ctcatgacca aaatccctta acgtgagtta cgcgcgcgtc gttccactga gcgtcagacc      60
ccgtagaaaa gatcaaagga tcttcttgag atcctttttt tctgcgcgta atctgctgct     120
tgcaaacaaa aaaaccaccg ctaccagcgg tggtttgttt gccggatcaa gagctaccaa     180
ctctttttcc gaaggtaact ggcttcagca gagcgcagat accaaatact gttcttctag     240
tgtagccgta gttagcccac cacttcaaga actctgtagc accgcctaca tacctcgctc     300
tgctaatcct gttaccagtg gctgctgcca gtggcgataa gtcgtgtctt accgggttgg     360
actcaagacg atagttaccg gataaggcgc agcggtcggg ctgaacgggg ggttcgtgca     420
cacagcccag cttggagcga acgacctaca ccgaactgag atacctacag cgtgagctat     480
gagaaagcgc cacgcttccc gaagggagaa aggcggacag gtatccggta agcggcaggg     540
tcggaacagg agagcgcacg agggagcttc caggggggaaa cgcctggtat ctttatagtc     600
ctgtcgggtt tcgccacctc tgacttgagc gtcgattttt gtgatgctcg tcagggggggc     660 ggagcctatg gaaaaacgcc agcaacgcgg cctttttacg gttcctggcc ttttgctggc     720
cttttgctca catgttcttt cctgcgttat cccctgattc tgtggataac cgtattaccg     780
cctttgagtg agctgatacc gctcgccgca gccgaacgac cgagcgcagc gagtcagtga     840
gcgaggaagc ggaagcgag agtagggaac tgccaggcat caaactaagc agaaggcccc     900
```

```
tgacggatgg cctttttgcg tttctacaaa ctctttctgt gttgtaaaac gacggccagt      960
cttaagctcg ggcccctgg gcggttctga taacgagtaa tcgttaatcc gcaaataacg     1020
taaaaacccg cttcggcggg ttttttatg gggggagttt agggaaagag catttgtcag     1080
aatatttaag ggcgcctgtc actttgcttg atatatgaga attatttaac cttataaatg     1140
agaaaaaagc aacgcacttt aaataagata cgttgctttt tcgattgatg aacacctata     1200
attaaactat tcatctatta tttatgattt tttgtatata caatatttct agtttgttaa     1260
agagaattaa gaaataaat ctcgaaaata ataagggaa aatcagtttt tgatatcaaa      1320
attatacatg tcaacgataa tacaaaatat aatacaaact ataagatgtt atcagtattt     1380
attatgcatt tagaataaat tttgtgtcgc ccttaattgt gagcggataa caattacgag     1440
cttcatgcac agtgaaatca tgaaaaattt atttgctttg tgagcggata acaattataa     1500
tatgtggaat tgtgagcgct cacaattcca caacggtttc cctctagaaa taattttgtt     1560
taacttttaa gaaggagata tacatatgcg gggttctcat caccatcacc atcacggtat     1620
ggctagcatg actggtggac agcaaatggg tcggcgatgg ggatccgagc tcgagatctg     1680
cagctggtac catggtactc gaagcagcag cggaggagga ggaagcggag gaggaggaag     1740
cggaggagga ggaagcaagt ctccagaaga actgaagggc attttcgaaa aatatgcagc     1800
caaagaaggt gatccaaacc aactgtccaa ggagagctg aagctactgc ttcagacgga      1860
attccccagt ttgctgaagg gtccatagcc ccaagggcga cacccctaa ttagcccggg      1920 cgaaaggccc agtctttcga ctgagccttt cgttttattt gatgcctggc agttccctac     1980
tctcgcatgg ggagtcccca cactaccatc ggcgctacgg cgtttcactt ctgagttcgg     2040 catgggggtca ggtgggacca ccgcgctact gccgccaggc aaacaagggg tgttatgagc    2100
catattcagg tataaatggg ctcgcgataa tgttcagaat tggttaattg gttgtaacac     2160 tgaccctat ttgttattt ttctaaatac attcaaatat gtatccgctc atgagacaat       2220
aaccctgata aatgcttcaa taatattgaa aaaggaagaa tatgagccat attcaacggg     2280
aaacgtcgag gccgcgatta aattccaaca tggatgctga tttatatggg tataaatggg     2340
ctcgcgataa tgtcgggcaa tcaggtgcga caatctatcg cttgtatggg aagcccgatg     2400
cgccagagtt gtttctgaaa catggcaaag gtagcgttgc caatgatgtt acagatgaga     2460
tggtcagact aaactggctg acggaattta tgccacttcc gaccatcaag cattttatcc     2520
gtactcctga tgatgcatgg ttactcacca ctgcgatccc cggaaaaaca gcgttccagg     2580
tattagaaga atatcctgat tcaggtgaaa atattgttga tgcgctggca gtgttcctgc     2640
gccggttgca ctcgattcct gtttgtaatt gtccttttaa cagcgatcgc gtatttcgcc     2700
tcgctcaggc gcaatcacga tgaataacg gtttggttga tgcgagtgat tttgatgacg     2760
agcgtaatgg ctggcctgtt gaacaagtct ggaaagaaat gcataaactt ttgccattct     2820
caccggattc agtcgtcact catggtgatt tctcacttga taaccttatt tttgacgagg     2880
ggaaattaat aggttgtatt gatgttggac gagtcggaat cgcagaccga taccaggatc     2940
ttgccatcct atggaactgc ctcggtgagt tttctccttc attacagaaa cggctttttc     3000
aaaaatatgg tattgataat cctgatatga ataaattgca gtttcatttg atgctcgatg     3060
agttttccta gcggcgcgc catcgaatgg cgcaaaacct ttcgcggtat ggcatgatag     3120
cgcccggaag agagtcaatt cagggtggtg aatatgaaac cagtaacgtt atacgatgtc     3180
gcagagtatg ccggtgtctc ttatcagacc gtttcccgcg tggtgaacca ggccagccac     3240
```

-continued

| | |
|---|---|
| gtttctgcga aaacgcggga aaaagtggaa gcggcgatgg cggagctgaa ttacattccc | 3300 |
| aaccgcgtgg cacaacaact ggcgggcaaa cagtcgttgc tgattggcgt tgccacctcc | 3360 |
| agtctggccc tgcacgcgcc gtcgcaaatt gtcgcggcga ttaaatctcg cgccgatcaa | 3420 |
| ctgggtgcca gcgtggtggt gtcgatggta gaacgaagcg cgtcgaagc ctgtaaagcg | 3480 |
| gcggtgcaca atcttctcgc gcaacgcgtc agtgggctga tcattaacta tccgctggat | 3540 |
| gaccaggatg ccattgctgt ggaagctgcc tgcactaatg ttccggcgtt atttcttgat | 3600 |
| gtctctgacc agacacccat caacagtatt attttctccc atgaggacgg tacgcgactg | 3660 |
| ggcgtggagc atctggtcgc attgggtcac cagcaaatcg cgctgttagc gggcccatta | 3720 |
| agttctgtct cggcgcgtct gcgtctggct ggctggcata aatatctcac tcgcaatcaa | 3780 |
| attcagccga tagcggaacg ggaaggcgac tggagtgcca tgtccggttt tcaacaaacc | 3840 |
| atgcaaatgc tgaatgaggg catcgttccc actgcgatgc tggttgccaa cgatcagatg | 3900 |
| gcgctgggcg caatgcgcgc cattaccgag tccgggctgc gcgttggtgc ggatatctcg | 3960 |
| gtagtgggat acgacgatac cgaagatagc tcatgttata tcccgccgtt aaccaccatc | 4020 |
| aaacaggatt ttcgcctgct ggggcaaacc agcgtggacc gcttgctgca actctctcag | 4080 |
| ggccaggcgg tgaagggcaa tcagctgttg ccagtctcac tggtgaaaag aaaaaccacc | 4140 |
| ctggcgccca atacgcaaac cgcctctccc cgcgcgttgg ccgattcatt aatgcagctg | 4200 |
| gcacgacagg tttcccgact ggaaagcggg cagtga | 4236 |

<210> SEQ ID NO 22
<211> LENGTH: 4852
<212> TYPE: DNA
<213> ORGANISM: Artificial
<220> FEATURE:
<223> OTHER INFORMATION: Plasmid

<400> SEQUENCE: 22

| | |
|---|---|
| ctcatgacca aaatccctta acgtgagtta cgcgcgcgtc gttccactga gcgtcagacc | 60 |
| ccgtagaaaa gatcaaagga tcttcttgag atcctttttt tctgcgcgta atctgctgct | 120 |
| tgcaaacaaa aaaaccaccg ctaccagcgg tggtttgttt gccggatcaa gagctaccaa | 180 |
| ctctttttcc gaaggtaact ggcttcagca gagcgcagat accaaatact gttcttctag | 240 |
| tgtagccgta gttagcccac cacttcaaga actctgtagc accgcctaca tacctcgctc | 300 |
| tgctaatcct gttaccagtg gctgctgcca gtggcgataa gtcgtgtctt accgggttgg | 360 |
| actcaagacg atagttaccg gataaggcgc agcggtcggg ctgaacgggg gttcgtgca | 420 |
| cacagcccag cttggagcga acgacctaca ccgaactgag atacctacag cgtgagctat | 480 |
| gagaaagcgc cacgcttccc gaagggagaa aggcggacag gtatccggta agcggcaggg | 540 |
| tcggaacagg agagcgcacg agggagcttc caggggggaaa cgcctggtat ctttatagtc | 600 |
| ctgtcgggtt tcgccacctc tgacttgagc gtcgattttt gtgatgctcg tcaggggggc | 660 |
| ggagcctatg gaaaaacgcc agcaacgcgg cctttttacg gttcctggcc ttttgctggc | 720 |
| cttttgctca catgttcttt cctgcgttat cccctgattc tgtggataac cgtattaccg | 780 |
| cctttgagtg agctgatacc gctcgccgca gccgaacgac cgagcgcagc gagtcagtga | 840 |
| gcgaggaagc ggaaggcgag agtagggaac tgccaggcat caaactaagc agaaggcccc | 900 |
| tgacggatgg ccttttttgcg tttctacaaa ctctttctgt gttgtaaaac gacggccagt | 960 |
| cttaagctcg ggcccctgg gcggttctga taacgagtaa tcgttaatcc gcaaataacg | 1020 |
| taaaaacccg cttcggcggg ttttttatg gggggagttt agggaaagag catttgtcag | 1080 |

```
aatatttaag ggcgcctgtc actttgcttg atatatgaga attatttaac cttataaatg    1140
agaaaaaagc aacgcacttt aaataagata cgttgctttt tcgattgatg aacacctata    1200
attaaactat tcatctatta tttatgattt tttgtatata caatatttct agtttgttaa    1260
agagaattaa gaaataaat ctcgaaaata ataaagggaa aatcagtttt tgatatcaaa     1320
attatacatg tcaacgataa tacaaaatat aatacaaact ataagatgtt atcagtattt    1380
attatcattt agaataaatt ttgtgtcgcc cttaattgtg agcggataac aattacgagc    1440
ttcatgcaca gtggcgttga cattgattat tgactagtta ttaatagtaa tcaattacgg    1500
ggtcattagt tcatagccca tatatggagt tccgcgttac ataacttacg gtaaatggcc    1560
cgcctggctg accgcccaac gacccccgcc cattgacgtc aataatgacg tatgttccca    1620
tagtaacgcc aatagggact ttccattgac gtcaatgggt ggagtattta cggtaaactg    1680
cccacttggc agtacatcaa gtgtatcata tgccaagtac gccccctatt gacgtcaatg    1740
acggtaaatg gcccgcctgg cattatgccc agtacatgac cttatgggac tttcctactt    1800
ggcagtacat ctacgtatta gtcatcgcta ttaccatggt gatgcggttt tggcagtaca    1860
tcaatgggcg tggatagcgg tttgactcac ggggatttcc aagtctccac cccattgacg    1920
tcaatgggag tttgttttgg caccaaaatc aacgggactt tccaaaatgt cgtaacaact    1980
ccgccccatt gacgcaaatg gcggtaggc gtgtacggtg ggaggtctat ataagcagag    2040
ctctctggct aactagagaa cccactgctt actggcttat cgaaattaat acgactcact    2100 atagggqtta agaaggagat atacatatgc ggggttctca tcaccatcac catcacggta    2160
tggctagcat gactggtgga cagcaaatgg gtcggaagtc tccagaagaa ctgaagggca    2220
ttttcgaaaa atatgcagcc aaagaaggtg atccaaacca actgtccaag gaggagctga    2280
agctactgct tcagacggaa ttccccagtt tgctgaaggg tccacgatgg ggatccgagc    2340
tcgagatctg cagctggtac catggtactc gaagcttgat ccggctgcta acaaagcccg    2400
aaaggaagct gagttggctg ctgccaccgc tgagcaataa ctagaaaatc agcctcgact    2460
gtgccttcta gttgccagcc atctgttgtt tgccctccc ccgtgccttc cttgaccctg    2520
gaaggtgcca ctcccactgt cctttcctaa taaaatgagg aaattgcatc acaacactca    2580
accctatctc ggtctattct tttgattat aagggatttt gccgatttcg gcctattggt    2640
taaaaaatga gctgatttaa caaaaattta acgcgaatta attctgtgga atgtgtgtca    2700
gttagggtgt ggaaagtccc caggctcccc agcaggcaga agtatgcaaa gcatgcatct    2760
caattagtca gcaaccaggt gtggaaagtc cccaggctcc ccagcaggca gaagtatgca    2820
aagcatgcat ctcaattagt cagcaaccat agtcccgccc ctaactccgc ccatcccgcc    2880
cctaactccg cccagttccg cccattctcc gccccatggc tgactaattt ttttattta    2940 tgcagaggcc gaggccgcct ctgcctctga gctattccag aagtagtgag gaggcttttt    3000
tggaggccta ggcttttgca aaagctcccg ggagcttgt atatccattt tcggatctga    3060
tcagcacgtg ttgacaatta atcatcggca tagtatatcg gcatagtata atacgacaag    3120
gtgaggaact aaaccatggc caagttgacc agtgccgttc cggtgctcac cgcgcgcgac    3180
gtcgccggag cggtcgagtt ctggaccgac cggctcgggt tctcccggga cttcgtggag    3240
gacgacttcg ccggtgtggt ccgggacgac gtgaccctgt tcatcagcgc ggtccaggac    3300
caggtggtgc cggacaacac cctggcctgg gtgtgggtgc gcggcctgga cgagctgtac    3360
gccgagtggt cggaggtcgt gtccacgaac ttccgggacg cctccgggcc ggccatgacc    3420
```

```
gagatcggcg agcagccgtg ggggcgggag ttcgccctgc gcgacccggc cggcaactgc    3480
gtgcacttcg tggccgagga gcaggactga cacgtgctac gagatttcga ttccaccgcc    3540
gccttctatg aaaggttggg cttcggaatc gttttccggg acgccggctg gatgatcctc    3600
cagcgcgggg atctcatgct ggagttcttc gcccacccca acttgtttat tgcagcttat    3660
aatggttaca aataaagcaa tagcatcaca aatttcacaa ataaagcatt ttttcactg     3720
cattctagtt gtggtttgtc caaactcatc aatgtatctt atcatgtctg tataccgtcg    3780
acctctagct agagcttggc gtaatcatgg tcattaccaa tgcttaatca gtgaggcacc    3840
tatctcagcg atctgtctat ttcgttcatc catagttgcc tgactccccg tcgtgtagat    3900
aactacgata cgggagggct taccatctgg ccccagcgct gcgatgatac cgcgagaacc    3960
acgctcaccg gctccggatt tatcagcaat aaaccagcca gccggaaggg ccgagcgcag    4020
aagtggtcct gcaactttat ccgcctccat ccagtctatt aattgttgcc gggaagctag    4080
agtaagtagt tcgccagtta atagtttgcg caacgttgtt gccatcgcta caggcatcgt    4140
ggtgtcacgc tcgtcgtttg gtatggcttc attcagctcc ggttcccaac gatcaaggcg    4200
agttacatga tcccccatgt tgtgcaaaaa agcggttagc tccttcggtc ctccgatcgt    4260
tgtcagaagt aagttggccg cagtgttatc actcatggtt atggcagcac tgcataattc    4320
tcttactgtc atgccatccg taagatgctt ttctgtgact ggtgagtact caaccaagtc    4380
attctgagaa tagtgtatgc ggcgaccgag ttgctcttgc ccggcgtcaa tacgggataa    4440
taccgcgcca catagcagaa ctttaaaagt gctcatcatt ggaaaacgtt cttcggggcg    4500
aaaactctca aggatcttac cgctgttgag atccagttcg atgtaaccca ctcgtgcacc    4560
caactgatct tcagcatctt ttactttcac cagcgtttct gggtgagcaa aacaggaag     4620
gcaaaatgcc gcaaaaaagg gaataagggc gacacgaaaa tgttgaatac tcatattctt    4680
cctttttcaa tattattgaa gcatttatca gggttattgt ctcatgagcg gatacatatt    4740
tgaatgtatt tagaaaaata aacaaatagg ggtcagtgtt acaaccaatt aaccaattct    4800
gaacattatc gcgagcccat ttataccga atatggctca taacacccct tg            4852
```

<210> SEQ ID NO 23
<211> LENGTH: 4837
<212> TYPE: DNA
<213> ORGANISM: Artificial
<220> FEATURE:
<223> OTHER INFORMATION: Plasmid

<400> SEQUENCE: 23

```
ctcatgacca aaatccctta acgtgagtta cgcgcgcgtc gttccactga gcgtcagacc      60
ccgtagaaaa gatcaaagga tcttcttgag atcctttttt tctgcgcgta atctgctgct     120
tgcaaacaaa aaaaccaccg ctaccagcgg tggtttgttt gccggatcaa gagctaccaa     180
ctctttttcc gaaggtaact ggcttcagca gagcgcagat accaaatact gttcttctag     240
tgtagccgta gttagcccac cacttcaaga actctgtagc accgcctaca tacctcgctc     300
tgctaatcct gttaccagtg ctgctgccag tggcgataag tcgtgtcttt accgggttgg     360
actcaagacg atagttaccg gataaggcgc agcggtcggg ctgaacgggg gttcgtgca      420
cacagcccag cttggagcga acgacctaca ccgaactgag atacctacag cgtgagctat     480
gagaaagcgc cacgcttccc gaagggagaa aggcggacag gtatccggta agcggcaggg     540
tcggaacagg agagcgcacg agggagcttc caggggggaaa cgcctggtat ctttatagtc     600
ctgtcgggtt tcgccacctc tgacttgagc gtcgattttt gtgatgctcg tcagggggc      660
```

```
ggagcctatg gaaaaacgcc agcaacgcgg ccttttttacg gttcctggcc ttttgctggc    720
cttttgctca catgttctttt cctgcgttat cccctgattc tgtggataac cgtattaccg    780
cctttgagtg agctgatacc gctcgccgca gccgaacgac cgagcgcagc gagtcagtga    840
gcgaggaagc ggaaggcgag agtagggaac tgccaggcat caaactaagc agaaggcccc    900
tgacggatgg ccttttttgcg tttctacaaa ctctttctgt gttgtaaaac gacggccagt    960
cttaagctcg ggcccctgg gcggttctga taacgagtaa tcgttaatcc gcaaataacg   1020
taaaaacccg cttcggcggg ttttttatg gggggagttt agggaaagag catttgtcag   1080
aatatttaag ggcgcctgtc actttgcttg atatatgaga attatttaac cttataaatg   1140
agaaaaaagc aacgcacttt aaataagata cgttgctttt tcgattgatg aacacctata   1200
attaaactat tcatctatta tttatgattt tttgtatata caatatttct agtttgttaa   1260
agagaattaa gaaataaat ctcgaaaata ataagggaa aatcagtttt tgatatcaaa   1320
attatacatg tcaacgataa tacaaaatat aatacaaact ataagatgtt atcagtattt   1380
attatcattt agaataaatt ttgtgtcgcc cttaattgtg agcggataac aattacgagc   1440
ttcatgcaca gtggcgttga cattgattat tgactagtta ttaatagtaa tcaattacgg   1500
ggtcattagt tcatagccca tatatggagt tccgcgttac ataacttacg gtaaatggcc   1560
cgcctggctg accgcccaac gacccccgcc cattgacgtc aataatgacg tatgttccca   1620
tagtaacgcc aatagggact ttccattgac gtcaatgggt ggagtattta cggtaaactg   1680
cccacttggc agtacatcaa gtgtatcata tgccaagtac gccccctatt gacgtcaatg   1740
acggtaaatg gcccgcctgg cattatgccc agtacatgac cttatgggac tttcctactt   1800
ggcagtacat ctacgtatta gtcatcgcta ttaccatggt gatgcggttt tggcagtaca   1860
tcaatgggcg tggatagcgg tttgactcac ggggatttcc aagtctccac cccattgacg   1920
tcaatgggag tttgttttgg caccaaaatc aacgggactt tccaaaatgt cgtaacaact   1980
ccgccccatt gacgcaaatg gcggtaggc gtgtacggtg ggaggtctat ataagcagag   2040
ctctctggct aactagagaa cccactgctt actggcttat cgaaattaat acgactcact   2100 atagggtta agaaggagat atacatatgc ggggttctca tcaccatcac catcacggta   2160
tggctagcat gactggtgga cagcaaatgg gtcggcgatg gggatccgag ctcgagatct   2220
gcagctggta ccatggtact cgaagcagca gcggaggagg aggaagcgga ggaggaggaa   2280
gcggaggagg aggaagcaag tctccagaag aactgaaggg cattttcgaa aaatatgcag   2340
ccaaagaagg tgatccaaac caactgtcca aggaggagct gaagctactg cttcagacgg   2400
aattccccag tttgctgaag gtccatagag aaaatcagcct cgactgtgcc ttctagttgc   2460
cagccatctg ttgtttgccc ctccccgtg ccttccttga ccctggaagg tgccactccc   2520
actgtccttt cctaataaaa tgaggaaatt gcatcacaac actcaaccct atctcggtct   2580
attcttttga tttataaggg attttgccga tttcggccta ttggtaaaa aatgagctga   2640 tttaacaaaa atttaacgcg aattaattct gtggaatgtg tgtcagttag ggtgtggaaa   2700
gtccccaggc tccccagcag gcagaagtat gcaaagcatg catctcaatt agtcagcaac   2760
caggtgtgga aagtccccag gctccccagc aggcagaagt atgcaaagca tgcatctcaa   2820
ttagtcagca accatagtcc cgcccctaac tccgcccatc ccgcccctaa ctccgcccag   2880
ttccgcccat tctccgcccc atggctgact aattttttt atttatgcag aggccgaggc   2940
cgcctctgcc tctgagctat tccagaagta gtgaggaggc ttttttggag gcctaggctt   3000
```

```
ttgcaaaaag ctcccgggag cttgtatatc cattttcgga tctgatcagc acgtgttgac    3060
aattaatcat cggcatagta tatcggcata gtataatacg acaaggtgag gaactaaacc    3120
atggccaagt tgaccagtgc cgttccggtg ctcaccgcgc gcgacgtcgc cggagcggtc    3180
gagttctgga ccgaccggct cgggttctcc cgggacttcg tggaggacga cttcgccggt    3240
gtggtccggg acgacgtgac cctgttcatc agcgcggtcc aggaccaggt ggtgccggac    3300
aacaccctgg cctgggtgtg ggtgcgcggc ctggacgagc tgtacgccga gtggcggag     3360
gtcgtgtcca cgaacttccg ggacgcctcc gggccggcca tgaccgagat cggcgagcag    3420
ccgtgggggc gggagttcgc cctgcgcgac cggccggca actgcgtgca cttcgtggcc     3480
gaggagcagg actgacacgt gctacgagat ttcgattcca ccgccgcctt ctatgaaagg    3540
ttgggcttcg gaatcgtttt ccgggacgcc ggctggatga tcctccagcg cggggatctc    3600
atgctggagt tcttcgccca ccccaacttg tttattgcag cttataatgg ttacaaataa    3660
agcaatagca tcacaaattt cacaaataaa gcatttttt cactgcattc tagttgtggt     3720
ttgtccaaac tcatcaatgt atcttatcat gtctgtatac cgtcgacctc tagctagagc    3780
ttggcgtaat catggtcatt accaatgctt aatcagtgag gcacctatct cagcgatctg    3840
tctatttcgt tcatccatag ttgcctgact ccccgtcgtg tagataacta cgatacggga    3900
gggcttacca tctggcccca gcgctgcgat gataccgcga gaaccacgct caccggctcc    3960
ggatttatca gcaataaacc agccagccgg aagggccgag cgcagaagtg gtcctgcaac    4020
tttatccgcc tccatccagt ctattaattg ttgccgggaa gctagagtaa gtagttcgcc    4080
agttaatagt ttgcgcaacg ttgttgccat cgctacaggc atcgtggtgt cacgctcgtc    4140
gtttggtatg gcttcattca gctccggttc ccaacgatca aggcgagtta catgatcccc    4200
catgttgtgc aaaaaagcgg ttagctcctt cggtcctccg atcgttgtca gaagtaagtt    4260
ggccgcagtg ttatcactca tggttatggc agcactgcat aattctctta ctgtcatgcc    4320
atccgtaaga tgcttttctg tgactggtga gtactcaacc aagtcattct gagaatagtg    4380
tatgcggcga ccgagttgct cttgcccggc gtcaatacgg gataataccg cgccacatag    4440
cagaacttta aaagtgctca tcattggaaa acgttcttcg gggcgaaaac tctcaaggat    4500
cttaccgctg ttgagatcca gttcgatgta acccactcgt gcacccaact gatcttcagc    4560
atcttttact ttcaccagcg tttctgggtg agcaaaaaca ggaaggcaaa atgccgcaaa    4620
aaagggaata agggcgacac ggaaatgttg aatactcata ttcttccttt ttcaatatta    4680
ttgaagcatt tatcagggtt attgtctcat gagcggatac atatttgaat gtatttagaa    4740
aaataaacaa ataggggtca gtgttacaac caattaacca attctgaaca ttatcgcgag    4800
cccatttata cctgaatatg gctcataaca ccccttg                            4837
```

<210> SEQ ID NO 24
<211> LENGTH: 337
<212> TYPE: DNA
<213> ORGANISM: Artificial
<220> FEATURE:
<223> OTHER INFORMATION: Plasmid

<400> SEQUENCE: 24

```
ttaagaagga gatatacata tgcggggttc tcatcaccat caccatcacg gtatggctag     60
catgactggt ggacagcaaa tgggtcggaa gtctccagaa gaactgaagg gcattttcga    120
aaaatatgca gccaaagaag gtgatccaaa ccaactgtcc aaggaggagc tgaagctact    180
gcttcagacg gaattcccca gtttgctgaa gggtccacga tggggatccg agctcgagat    240
```

```
ctgcagctgg taccatggta ctcgaagctt gatccggctg ctaacaaagc ccgaaaggaa    300
gctgagttgg ctgctgccac cgctgagcaa taactag                             337

<210> SEQ ID NO 25
<211> LENGTH: 322
<212> TYPE: DNA
<213> ORGANISM: Artificial
<220> FEATURE:
<223> OTHER INFORMATION: Plasmid

<400> SEQUENCE: 25
ttaagaagga gatatacata tgcggggttc tcatcaccat caccatcacg gtatggctag     60
catgactggt ggacagcaaa tgggtcggcg atggggatcc gagctcgaga tctgcagctg    120
gtaccatggt actcgaagca gcagcggagg aggaggaagc ggaggaggag gaagcggagg    180
aggaggaagc aagtctccag aagaactgaa gggcattttc gaaaaatatg cagccaaaga    240
aggtgatcca aaccaactgt ccaaggagga gctgaagcta ctgcttcaga cggaattccc    300
cagtttgctg aagggtccat ag                                            322

<210> SEQ ID NO 26
<211> LENGTH: 337
<212> TYPE: DNA
<213> ORGANISM: Artificial
<220> FEATURE:
<223> OTHER INFORMATION: Plasmid

<400> SEQUENCE: 26
ttaagaagga gatatacata tgcggggttc tcatcaccat caccatcacg gtatggctag     60
catgactggt ggacagcaaa tgggtcggaa gtctccagaa gaactgaagg cattttcga    120 aaaatatgca gccaaagaag gtgatccaaa ccaactgtcc aaggaggagc tgaagctact    180
gcttcagacg gaattcccca gtttgctgaa gggtccacga tggggatccg agctcgagat    240
ctgcagctgg taccatggta ctcgaagctt gatccggctg ctaacaaagc ccgaaaggaa    300
gctgagttgg ctgctgccac cgctgagcaa taactag                             337

<210> SEQ ID NO 27
<211> LENGTH: 322
<212> TYPE: DNA
<213> ORGANISM: Artificial
<220> FEATURE:
<223> OTHER INFORMATION: Plasmid

<400> SEQUENCE: 27
ttaagaagga gatatacata tgcggggttc tcatcaccat caccatcacg gtatggctag     60
catgactggt ggacagcaaa tgggtcggcg atggggatcc gagctcgaga tctgcagctg    120
gtaccatggt actcgaagca gcagcggagg aggaggaagc ggaggaggag gaagcggagg    180
aggaggaagc aagtctccag aagaactgaa gggcattttc gaaaaatatg cagccaaaga    240
aggtgatcca aaccaactgt ccaaggagga gctgaagcta ctgcttcaga cggaattccc    300
cagtttgctg aagggtccat ag                                            322

<210> SEQ ID NO 28
<211> LENGTH: 21
<212> TYPE: DNA
<213> ORGANISM: Artificial
<220> FEATURE:
<223> OTHER INFORMATION: Primer
```

```
<400> SEQUENCE: 28
tggggatcca tggccgaaga c                                                  21

<210> SEQ ID NO 29
<211> LENGTH: 24
<212> TYPE: DNA
<213> ORGANISM: Artificial
<220> FEATURE:
<223> OTHER INFORMATION: Primer

<400> SEQUENCE: 29
atcccatggt taaccacttc ccag                                               24

<210> SEQ ID NO 30
<211> LENGTH: 263
<212> TYPE: DNA
<213> ORGANISM: Artificial
<220> FEATURE:
<223> OTHER INFORMATION: Plasmid

<400> SEQUENCE: 30
aggagataaa acatatgaaa tacctattgc ctacggcagc cgctggattg ttattactcg        60
cggcccagcc ggccatggcc gagatgaccc aggcggccgc aggcggttct ggttccggta       120
gcagcaagag cccggaagag ctgaaaggca tcttcgagaa gtatgcggcg aaagagggcg       180
acccgaacca actgagcaaa gaagaactga agctgctgct gcaaaccgag tttccgagcc       240
tgctgaaggg tatgtaactc gag                                              263

<210> SEQ ID NO 31
<211> LENGTH: 126
<212> TYPE: DNA
<213> ORGANISM: Artificial
<220> FEATURE:
<223> OTHER INFORMATION: EF1 hand subdomain

<400> SEQUENCE: 31
aagagcccgg aagagctgaa aggcatcttc gagaagtatg cggcgaaaga gggcgacccg        60
aaccaactga gcaaagaaga actgaagctg ctgctgcaaa ccgagtttcc gagcctgctg       120
aagggt                                                                 126

<210> SEQ ID NO 32
<211> LENGTH: 126
<212> TYPE: DNA
<213> ORGANISM: Artificial
<220> FEATURE:
<223> OTHER INFORMATION: EF1 hand subdomain

<400> SEQUENCE: 32
aagtctccag aagaactgaa gggcattttc gaaaaatatg cagccaaaga aggtgatcca        60
aaccaactgt ccaaggagga gctgaagcta ctgcttcaga cggaattccc cagtttgctg       120
aagggt                                                                 126
```

AFFINITY TAG SYSTEM

CROSS REFERENCE TO RELATED APPLICATION

The present application is the U.S. national stage of International Application PCT/EP2013/050169, filed Jan. 7, 2013, which international application was published on Jul. 11, 2013, as International Publication No. WO2013102684. The International Application claims priority to European Patent Application No. 12150412.0, filed Jan. 6, 2012, the contents of which are incorporated herein by reference in their entireties.

FIELD OF THE INVENTION

The present invention relates to an affinity tag system for the immobilisation, detection and/or purification of molecules. Particularly, although not exclusively, the invention relates to the use of EF-hand subdomains of calcium-binding proteins, such as the EF1 and EF2 subdomains of calbindin D9k, as affinity tags and cognate affinity ligands for the immobilisation, detection and/or purification of proteins and other molecules.

BACKGROUND TO THE INVENTION

The ability to 'tether' or 'immobilise' small molecules at a desired location is important for numerous applications. For example, in biological systems, the immobilisation of proteins at a solid substrate may be used to isolate and/or detect specific proteins within a complex biological sample. Moreover, the tethering of a protein to a substrate is often used to achieve separation or purification of proteins from a mixture of biological molecules, for example a cell lysate.

Several approaches exist for the immobilisation, detection and purification of biological molecules, including proteins. For example, antibodies may be exploited to purify their respective antigens by immunoprecipitation. Proteins may also be purified using alternative affinity purification techniques, wherein an "affinity ligand" capable of binding to the protein of interest is typically used to isolate the protein.

For the purposes of affinity purification, the protein of interest is often "tagged" with a molecule to which an affinity ligand specifically binds. Several molecular tagging systems have been developed and used to generate fusion proteins incorporating tags including the following: myc tag; Flag-peptide tag; His Tag; Strep-Tag; GST-Tag; MBP-Tag; SNAP-Tag; Halo-Tag; Tap-Tag; INPACT-CN. The cognate affinity ligands for each of these tags are known and can be used, for example, in the context of affinity chromatography approaches, for the isolation of tagged proteins of interest.

Despite the availability of several commercial molecular tagging systems, there are disadvantages associated with many of the existing tags. In particular, the size of the tag can create problems during production of the recombinant fusion protein, such as the formation of inclusion bodies, difficulty in solubilisation, lack of stability and/or incorrect folding of the fusion protein and non-specific purification of bacterial proteins. Moreover, it has been reported that metal containing resins that bind His-Tags promote non-specific oxidation on amino acid side chains of the protein during purification. This oxidation often affects protein functionality.

An additional challenge in the field of molecular or affinity tags used for the purposes of protein purification is to balance the strength and specificity of binding needed to achieve efficient purification with a sufficiently low-affinity interaction that can be dissociated so as to elute the purified protein. If the strength of binding between the tag of the fusion protein and its cognate affinity ligand is too high, a harsh elution protocol may be required to release the protein, and this may significantly impair the function of the purified protein.

SUMMARY OF THE INVENTION

The present inventors sought to exploit calcium-dependent interactions between fragments or regions of naturally-occurring proteins in order to develop a new affinity tag system, which overcomes many of the disadvantages associated with the existing systems. The molecular/affinity tags and affinity ligand 'binding pairs' of the present invention are based upon EF-hand subdomains found in many calcium-binding proteins.

In accordance with a first aspect of the invention, there is provided an affinity tag system for immobilizing a molecule, said system comprising:
  (i) an affinity matrix comprising a first EF-hand subdomain or fragment thereof attached to a substrate; and
  (ii) a molecule tagged with a second EF-hand subdomain or fragment thereof,
wherein the molecule is immobilized at the substrate via the interaction between the first and second EF-hand subdomains or fragments thereof.

The first EF-hand subdomain or fragment thereof will typically bind the second EF-hand subdomain or fragment thereof in the presence of calcium.

A fragment of a first or second EF-hand subdomain may be any fragment which retains the ability of the full-length EF-hand subdomain to form an EF-hand binding pair.

In accordance with a second aspect of the invention, there is provided an affinity matrix comprising a first EF-hand subdomain or fragment thereof that is capable of binding to a second EF-hand subdomain in the presence of calcium, wherein said first EF-hand subdomain or fragment thereof is attached to a substrate.

Also provided herein is a fusion protein comprising an EF-hand subdomain and a polypeptide sequence that is not part of the EF-hand subdomain. Isolated polynucleotide sequences encoding said fusion protein, expression vectors comprising such polynucleotide sequences, and host cells comprising such expression vectors are further provided.

In a further aspect of the invention, there is provided a method for detecting the presence of a biological molecule tagged with an EF-hand subdomain or a fragment thereof in a sample, said method comprising the steps of:
  (i) providing an affinity matrix according to the second aspect of the present invention;
  (ii) bringing a sample containing the tagged biological molecule into contact with the affinity matrix of (i) under conditions that permit binding of the EF-hand subdomains; and
  (iii) detecting the presence of the biological molecule attached to the affinity matrix.

In a further aspect of the invention, there is provided a method for purifying a biological molecule tagged with an EF-hand subdomain or a fragment thereof from a sample, said method comprising the steps of:
  (i) providing an affinity matrix according to the second aspect of the invention;
  (ii) bringing a sample containing the tagged biological molecule into contact with the affinity matrix of (i) under conditions that permit binding of the EF-hand subdomains;

(iii) separating any unbound material from the tagged biological molecule bound to the affinity matrix; and
(iv) effecting release of the tagged biological molecule from the affinity matrix.

In the methods of the invention, the EF-hand subdomains, or fragments thereof will typically bind in the presence of calcium. A fragment of the EF-hand subdomain tag may be any fragment which retains the ability of the full-length EF-hand subdomain to form an EF-hand binding pair with the EF-hand affinity ligand.

A Fusion protein purification using EF2-silica nanoparticles: (1) native lysate of EF1-Snap25 (2) first calcium wash (3) second calcium wash (4) elution of EF1-Snap25 in EDTA buffer.

B Confirmation of fusion protein expression with 6×His tag: (1) no fusion protein expression from empty vector (2) denatured lysate of EF1-Snap25 (3) native lysate of EF1-Snap25 (4) flow through from Ni-NTA column (5) elution of EF1-Snap25 fusion protein in 250 mM imidazole.

Figure 4:
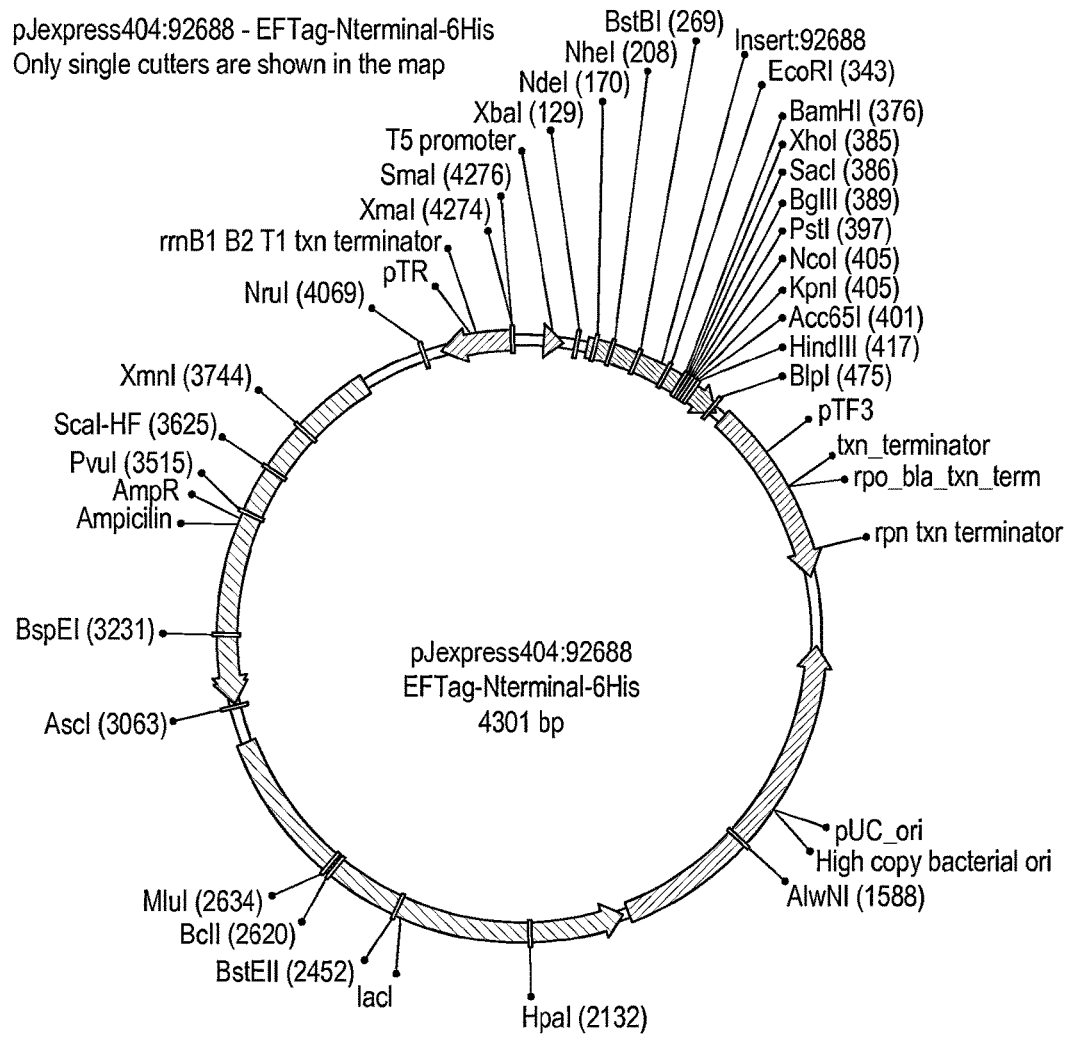

FIG. 4 Plasmid map for pJexpress404:92688 (EFTag-Nterminal-6His)

Figure 5:
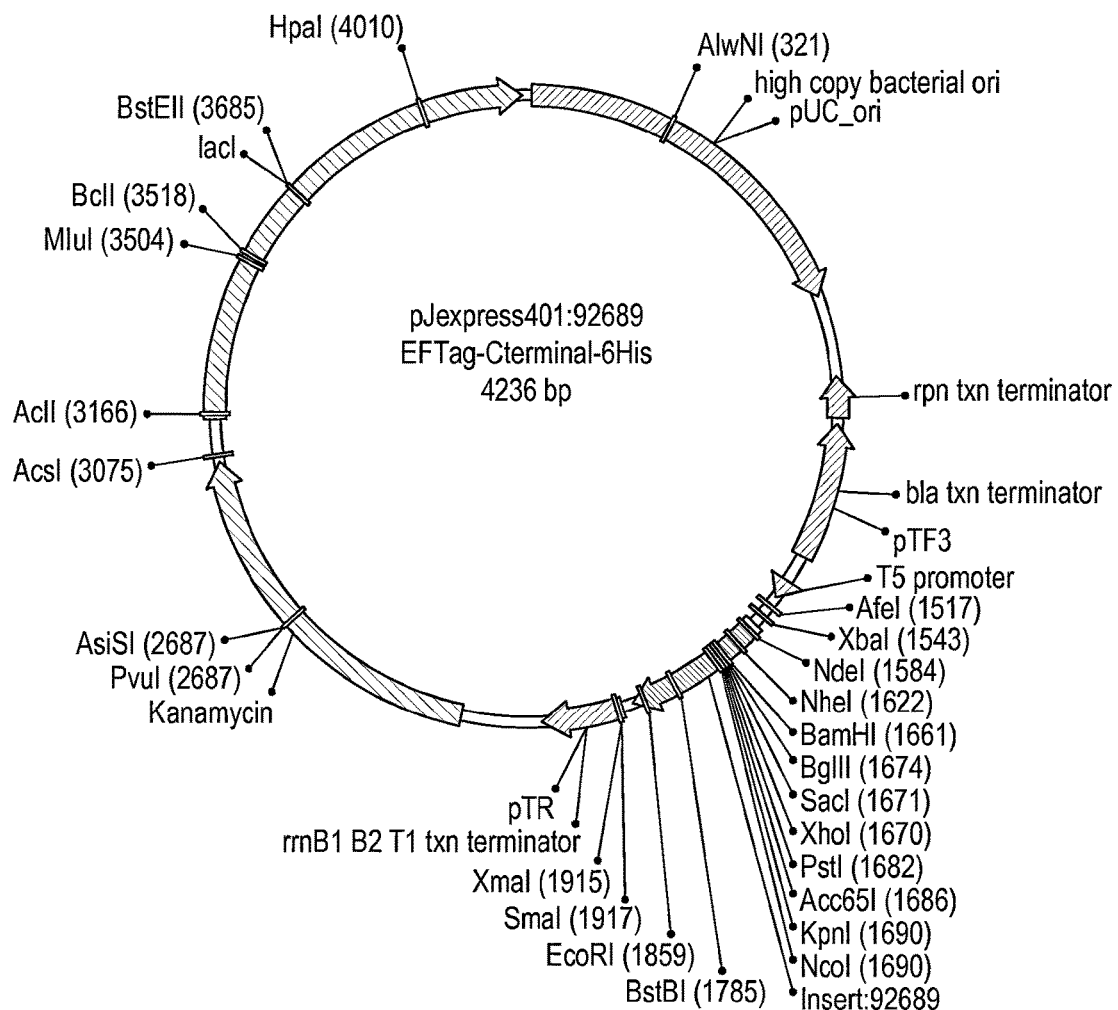

FIG. 5 Plasmid map for pJexpress401:92689 (EFTag-Cterminal-6His)

Figure 6:
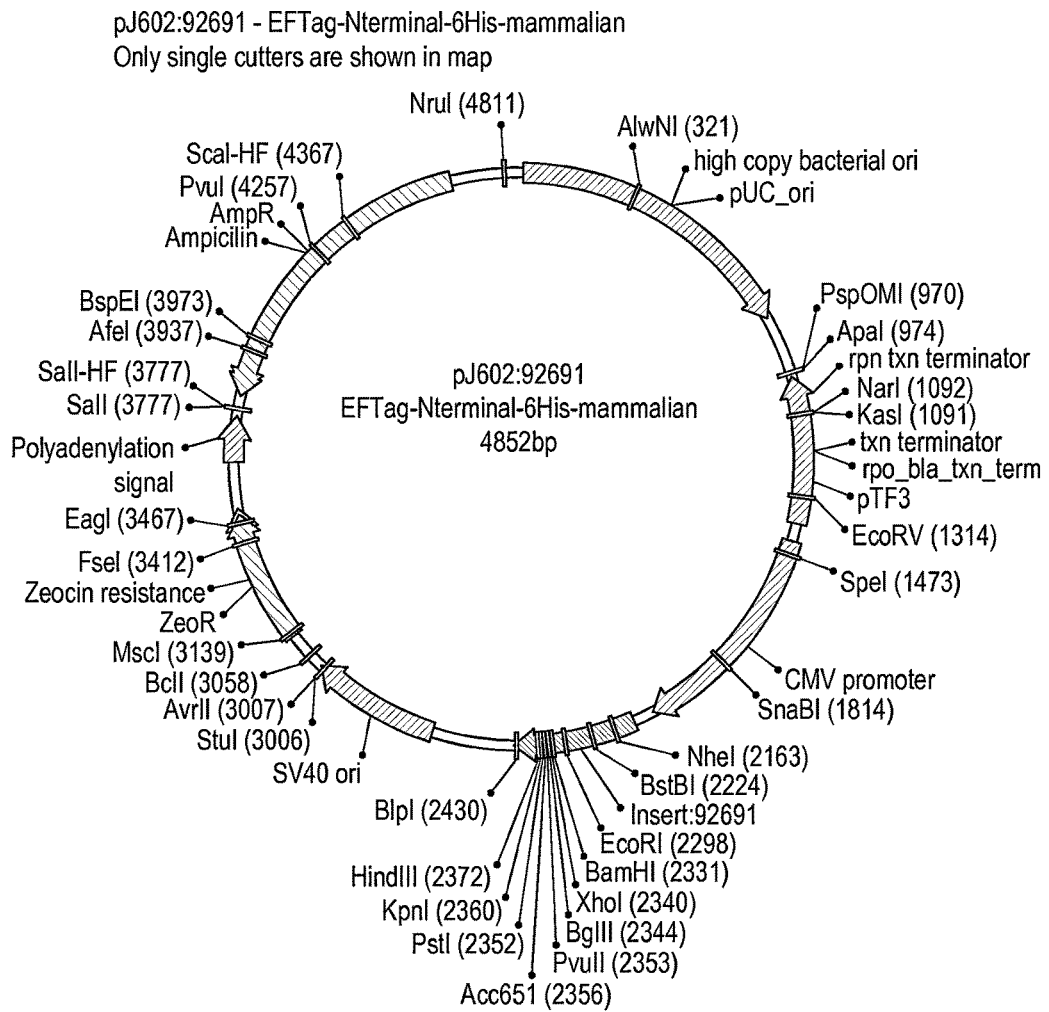

FIG. 6 Plasmid map for pJ602:92691 (EFTag-Nterminal-6His-mammalian)

Figure 7:
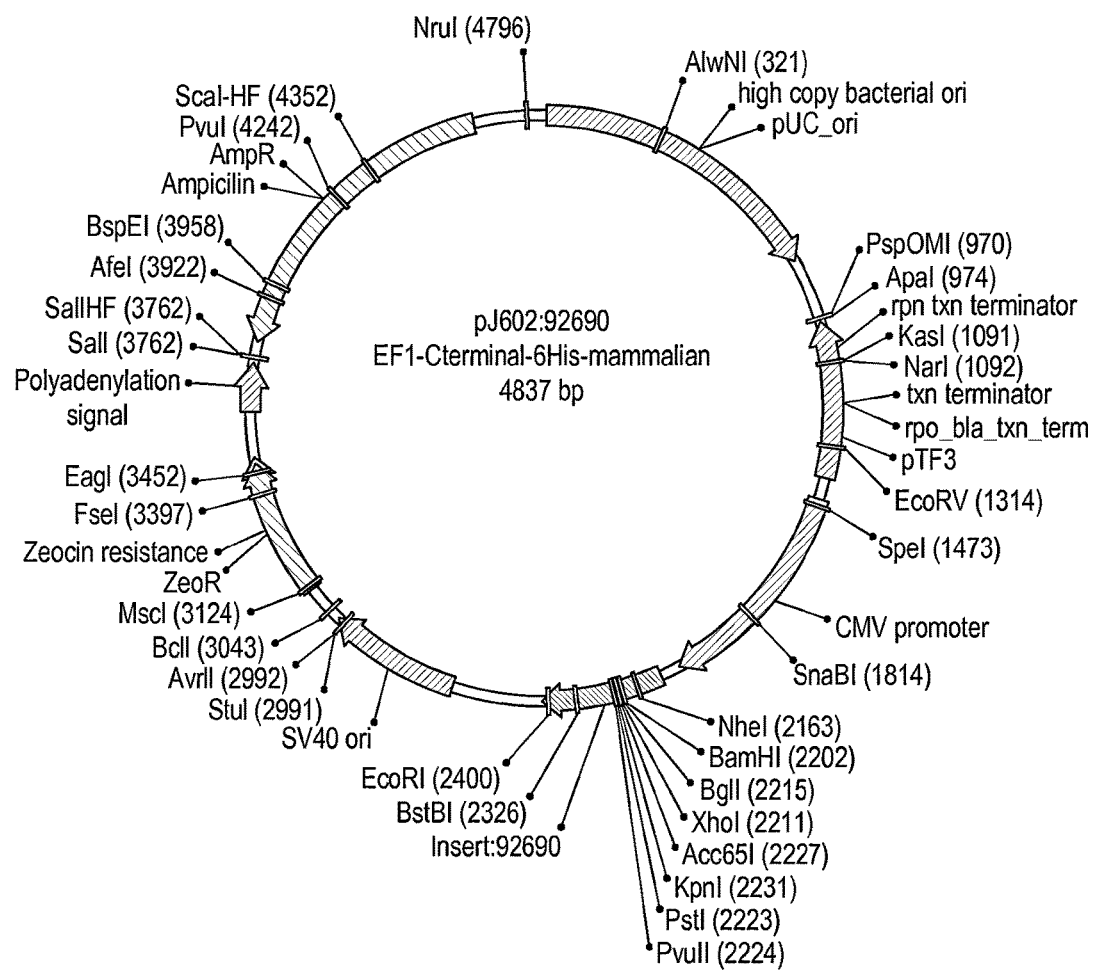

FIG. 7 Plasmid map for pJ602:92690 (EF1-Cterminal-6His-mammalian)

DETAILED DESCRIPTION

EF-Hands as Affinity Tags/Affinity Ligands

The present invention provides an affinity tag system based on the use of EF-hand subdomains. The system of the invention is based on two components: (i) an affinity matrix comprising a first EF-hand subdomain or fragment thereof attached to a substrate; and (ii) a molecule tagged with a second EF-hand subdomain or fragment thereof.

EF-hand subdomains are discrete regions of conserved 3-dimensional structure found in many calcium binding proteins such as calmodulin 1 (SEQ ID NO: 3), calmodulin 2 (SEQ ID NO: 4), calmodulin 3 (SEQ ID NO: 5), calmodulin-like 3 (SEQ ID NO: 6), calmodulin-like 5 (SEQ ID NO: 7), calmodulin-like 6 (SEQ ID NO: 8), calbindin 1 (SEQ ID NO: 9), calbindin 2 (SEQ ID NO: 10), calbindin D9K (SEQ ID NO: 11), recoverin (SEQ ID NO: 12), frequenin (SEQ ID NO: 13), troponin C (SEQ ID NO: 14), parvalbumin (SEQ ID NO: 15), calbindin D28k (SEQ ID NO: 16), secretagogin (SEQ ID NO: 17) and calretinin (SEQ ID NO: 18).

The underlying amino acid sequences of protein regions defined as "EF-hand subdomains" can vary considerably. However, EF-hand subdomains are typically characterised by a conserved "helix-loop-helix" secondary structure protein motif. The crystal structures of many EF-hand containing proteins have been solved (Håkansson M. et al. An extended hydrophobic core induces EF-hand swapping. *Protein Science* (2001), 10: 927-933).

It is a requirement of the present invention that the first EF-hand subdomain and the second EF-hand subdomain of the affinity tag system form a "binding pair". As used herein, the term binding pair means two molecules or entities that are capable of interacting or associating so as to form a binding complex. It is preferable that the binding interaction between the binding pair is specific such that each member of the binding pair is only able to bind its respective partner, or a limited number of binding partners. EF-hand subdomains for use in conjunction with the present invention include EF-hand subdomains selected from any calcium-binding protein that are capable of forming a binding pair with a second EF-hand subdomain. The first and second EF-hand subdomains that make up the binding pair of the present affinity tag system may derive from different calcium binding proteins, but are preferably derived from the same calcium binding protein.

The calcium-binding protein may be selected from any suitable source including proteins of human, bovine, murine or rat origin. EF-hand subdomains may also derive from proteins having at least 70%, 75%, 80%, 85%, 90% or 95% identity to calcium-binding proteins of human, bovine, murine or rat origin. The proteins from which the EF-hand subdomains derive may be purified proteins, recombinantly-expressed proteins or chemically-synthesised proteins.

In certain embodiments, the first and second EF-hand subdomains are non-identical and derive from the same calcium binding protein, wherein said calcium binding protein contains at least two different EF-hand subdomains.

The first and second EF-hand subdomains typically bind to each other in the presence of calcium. EF-hand subdomains that form binding pairs suitable for use in the affinity tag system of the present invention may therefore be identified by taking a calcium binding protein containing at least two EF-hand subdomains, fragmenting said protein so as to produce at least two fragments, each fragment containing at least one EF-hand subdomain, and attempting to reconstitute the protein from the respective fragments in a calcium-dependent manner. Fragments that permit reconstitution of the protein in the presence of calcium or that permit the non-covalent association of at least two fragments of the original protein in the presence of calcium, are suitable sources of EF-hand subdomains for use in the affinity tag system of the present invention.

Typically, the affinity of binding between the first EF-hand subdomain and the second EF-hand subdomain of the affinity tag system in the presence of calcium comprises a $K_D$ less than 1 µM, preferably less than 100 nM and more preferably less than 10 nM. The binding affinity between the first EF-hand subdomain and the second EF-hand subdomain may be in the nM, pM or fM range.

In a preferred embodiment of the invention, the first and second EF-hand subdomains derive from the calcium-binding protein calbindin D9k. Calbindin D9k (also known as S100 calcium binding protein) is a small (Mr 8500) calcium binding protein consisting of two EF-hand subdomains, EF1 and EF2. EF1 and EF2 interact with high affinity ($K_A=1.3\times 10^{10}$ M$^{-1}$; $K_D=80$ pM) and therefore calbindin D9k can be reconstituted in vitro from two separate protein fragments corresponding to its EF1 and EF2 domains.

In the present invention, the first EF-hand subdomain of the binding pair forms at least part of the "affinity ligand" attached to the substrate of the affinity matrix. The second EF-hand subdomain forms at least part of the tag or molecular tag or affinity tag attached to a molecule of interest.

In certain embodiments of the invention, the first EF-hand subdomain comprises the amino acid sequence as follows:

(SEQ ID NO: 1)
STLDELFEELDKNGDGEVSFEEFQVLVKKISQ or a fragment thereof as described herein.

In further embodiments, the first EF-hand subdomain comprises an amino acid sequence with at least 70%, 75%, 80%, 85%, 90%, 95% sequence identity to SEQ ID NO: 1.

As used herein, the term "sequence identity" is used to describe the sequence relationship between two or more nucleotide or amino acid sequences. The percentage of "sequence identity" between two sequences is determined by comparing two optimally aligned sequences over a comparison window (a defined number of positions), wherein the portion of the sequence in the comparison window may comprise additions or deletions (i.e. gaps) as compared to the reference sequence in order to achieve optimal alignment. The percentage sequence identity is calculated by determining the number of positions at which the identical nucleotide base or amino acid residue occurs in both sequences to yield the number of 'matched' positions, dividing the number of matched positions by the total number of positions in the comparison window and multiplying the result by 100. For comparison of two optimally aligned sequences, the comparison window will be determined by the full length of the aligned regions. Methods and software for determining sequence identity are available in the art and include the Blast software and GAP analysis. Sequences may be aligned using any of the algorithms available within the sequence alignment tools, including algorithms utilising standard parameters such as the megablast, discontinuous megablast or blastn algorithms for aligning nucleotide sequences or the PSI-BLAST, PHI-BLAST or blastp algorithms for aligning protein sequences, available via the Blast software.

In certain embodiments of the invention, the second EF-hand subdomain comprises the amino acid sequence as follows:

(SEQ ID NO: 2)
KSPEELKGIFEKYAAKEGDPNQLSKEELKLLLGTEFPSLLKGM or a fragment thereof as described herein.

In further embodiments, the second EF-hand subdomain comprises an amino acid sequence with at least 70%, 75%, 80%, 85%, 90%, 95% sequence identity to SEQ ID NO: 2.

In certain embodiments of the invention, the second EF-hand subdomain may be encoded by a polynucleotide as represented by SEQ ID NO: 31 or SEQ ID NO: 32 or a polynucleotide with at least 70%, 75%, 80%, 85%, 90%, 95% sequence identity thereto. Expression vectors incorporating a polynucleotide sequence encoding a second EF-hand subdomain are as described elsewhere herein.

The EF-hand subdomains for use in conjunction with the affinity tag system of the present invention may represent native or wild-type forms such as subdomains isolated from native or wild-type forms of calcium-binding proteins. Alternatively, modified EF-hand subdomains may be used, so long as sufficient binding affinity between the EF-hand subdomain of the affinity matrix (the first EF-hand subdomain) and the EF-hand subdomain of the affinity tag (the second EF-hand subdomain) is retained. As used herein, the binding affinity between the EF-hand subdomains is sufficient, if the $K_D$ is less than 1 µM, preferably less than 100 nM and more preferably less than 10 nM.

Modifications of the EF-hand subdomains may include deletion of amino acid residues, insertion of amino acid residues, point mutations and/or concatenations. Point mutations may include missense mutations wherein any amino acid within an EF-hand subdomain is substituted for any other amino acid. In certain embodiments, conservative substitutions may be introduced wherein a conservative substitution involves the substitution of one amino acid for another amino acid of the same category, i.e. acidic, basic, hydrophobic and hydrophilic. A conservative substitution may be introduced so as to preserve the overall charge of the EF-hand subdomain.

A person skilled in the art will recognise that modifications may be made for a number of reasons. These may include modifications to enhance or reduce the affinity of binding between the EF-hand subdomains, modifications to improve the stability of the EF-hand subdomain or the molecule to which it is attached, modifications to facilitate attachment of the first EF-hand subdomain of the affinity ligand to the substrate of the affinity matrix or to facilitate attachment of the second EF-hand subdomain of the affinity tag to the molecule of interest.

Modified EF-hand subdomains may have varying levels of sequence identity with the corresponding wild-type form of the EF-hand subdomain. In certain embodiments, a modified EF-hand subdomain may have at least 70%, 75%, 80%, 85%, 90% or 95% identity to the corresponding wild-type form of the EF-hand subdomain.

In certain embodiments, the affinity tag system of the present invention may comprise an affinity matrix comprising a fragment of a first EF-hand domain attached to a substrate. In alternative or additional embodiments, the affinity tag system of the present invention may comprise a molecule tagged with a fragment of a second EF-hand domain.

As used herein, the term fragment should be taken to mean a region of an EF-hand subdomain that is shorter in length as compared with the full-length EF-hand subdomain by 1, 2, 3, 4, 5 etc amino acids. It is however, a requirement of the present invention that any EF-hand subdomain fragments used as part of the affinity tag system of the present invention retain the ability of the full-length EF-hand subdomain to form an EF-hand binding pair. Therefore, a fragment of a first or second EF-hand subdomain may be any fragment which retains the ability of the full-length EF-hand subdomain to form an EF-hand binding pair. The binding affinity of such EF-hand subdomain fragments may be enhanced or reduced as compared with the corresponding full-length EF-hand subdomains.

EF-Hand Affinity Matrix

The first component of the affinity tag system of the present invention is an "affinity matrix". As used herein, the term affinity matrix refers to a substrate to which an affinity ligand is attached. The affinity ligand comprises a first EF-hand subdomain or fragment thereof in accordance with the description above; this is referred to herein as the EF-hand affinity ligand. The EF-hand affinity ligand is capable of binding to the second EF-hand subdomain "tag" attached to the molecule of interest and is therefore capable of immobilising the molecule at the substrate of the affinity matrix. Binding of the EF-hand affinity ligand to the second EF-hand subdomain tag typically occurs in the presence of calcium. Binding of the EF-hand tagged molecule may occur at calcium concentrations exceeding 10 nM.

In a preferred embodiment, the first EF-hand subdomain of the affinity ligand comprises the amino acid sequence of SEQ ID NO:1 or an amino acid sequence with at least 70%, 75%, 80%, 85%, 90%, 95% sequence identity to SEQ ID NO: 1.

In addition to a first EF-hand subdomain, the affinity ligand may include additional amino acid residues. For example, the affinity ligand may include additional polypeptide sequences or fragments that flank the EF-hand subdomain in the context of the wild-type protein from which the EF-hand subdomain derives. The affinity ligand may also include additional EF-hand subdomains, for example, one or more, two or more, three or more and so on, EF-hand subdomains. Additional amino acid residues and/or subdomains may be included in the affinity ligand for a number of reasons, for example to increase the affinity of the affinity ligand for the second EF-hand subdomain tag attached to the molecule of interest.

The substrate of the affinity matrix may consist of any suitable material but is preferably solid. In certain embodiments, the substrate may include but is not limited to cross-linked polysaccharides such as cellulose, dextran (sephadex), agarose, sepharose, paper, glass, plastic, metal, minerals, ceramics, cellulose, semiconductive materials, silica, various membranes (porous or non-porous) or rigid polymeric resins such as polystyrene, polystyrene/latex, and other organic and inorganic polymers, both natural and synthetic. Substances that form gels, such as proteins (e.g. gelatins), lipopolysaccharides, silicates, agarose, and polyacrylamides can also be used. Polymers such as dextrans, polyalkylene glycols or surfactants, such as phospholipids or long chain (12-24 carbon atoms) alkyl ammonium salts are also suitable.

The substrate may take any of a number of forms. These include but are not limited to solid or porous beads or other particles, solid surfaces such as array substrates, columns, capillaries and the like. In a preferred embodiment of the invention, the substrate comprises nanoparticles, such as silica nanoparticles. As used herein, the term "nanoparticle" should be taken to mean a microscopic particle with at least one dimension less than 100 nm. In certain embodiments, the substrate is not a sensor chip of the type used in conjunction with the BIACORE® 3000 apparatus.

Moreover, the substrate may be attached to a further support such that the affinity matrix adopts a suitable form for the required application. For example, the substrate may be packed into a column, a capillary, a microcapillary or an electrophoresis tube to form an affinity matrix through which a sample can pass. Alternatively, the substrate may be used to line the walls of a vessel or the wells of a multiwell plate to which a sample containing the tagged molecule of interest is added.

The EF-hand affinity ligand may be attached to the substrate via any suitable means. In one embodiment, the ligand is covalently attached to the substrate. If the EF-hand affinity ligand is to be covalently bound to the substrate of the affinity matrix, the substrate can be polyfunctional or capable of being polyfunctionalized. Functional groups that can be present on the substrate and used for linking include but are not limited to carboxylic acids, aldehydes, amino groups, cyano groups, ethylenic groups, hydroxyl groups, mercapto groups and haloacetyl groups (i.e. iodoacetyl groups). The EF-hand affinity ligand may be attached to the substrate directly. In one embodiment, the ligand is attached to the substrate via random amine coupling mediated by any amino acid along the length of the EF-hand subdomain, provided that this does not interfere with binding of the EF-hand affinity ligand to the second EF-hand subdomain tag. In a further embodiment, the EF-hand affinity ligand incorporates a cysteine residue at the N-terminus or C-terminus and the first EF-hand affinity ligand is attached to the substrate via thiol coupling.

The EF-hand affinity ligand may also be attached to the substrate indirectly, for example by means of a cross-linking reagent or linker. Suitable cross-linking reagents would be known to one of skill in the art and include, but are not limited to carbodiimides, maleimides, succinamides and reactive disulfides. Suitable linkers are also known and include but are not limited to alkyl chains such as straight or branched-chain carbon linkers, heterocyclic carbon linkers, carbohydrate linkers and polypeptide linkers.

EF-Hand Tagged Molecules

The second component of the affinity tag system of the present invention is a molecule tagged with a second EF-hand subdomain or fragment thereof. As used herein, a 'tag' is a molecule attached to the molecule of interest. In the present invention, the tag comprises an EF-hand subdomain or fragment thereof according to any of the embodiments described above; the tag will therefore be referred to herein as the "EF-hand tag". An "EF-hand tagged" molecule or "tagged" molecule is any molecule to which an EF-hand tag of the invention is attached so as to form a chimeric molecule.

In addition to an EF-hand subdomain, the affinity tag may include additional amino acid residues. For example, the affinity tag may include additional polypeptide sequences or fragments that flank the EF-hand subdomain in the context of the wild-type protein from which the EF-hand subdomain derives. The affinity tag may also include additional EF-hand subdomains, for example, one or more, two or more, three or more and so on, EF-hand subdomains. Additional amino acid residues and/or subdomains may be included in the affinity tag for a number of reasons, for example to increase the affinity of the affinity tag for the EF-hand affinity ligand of the affinity matrix.

The molecule to which the EF-hand tag is attached may be any organic or biological molecule of interest including but not limited to a protein, a polypeptide, a nucleic acid, a lipid, a polysaccharide, a carbohydrate and a lectin. In a preferred embodiment, the EF-hand tag is attached to a polypeptide or protein sequence that is not part of the EF-hand subdomain, to form a fusion protein.

The EF-hand tag may be attached to the molecule of interest by any suitable means, and may be attached directly or indirectly. Wherein the molecule is a protein or polypeptide, the EF-hand tag may be covalently attached to the polypeptide sequence at the N-terminus of the polypeptide sequence or at the C-terminus of the polypeptide sequence. Alternatively, the EF-hand tag may be attached to the side chain functional group of an amino acid residue of the polypeptide sequence at a position between the N-terminus and C-terminus of the polypeptide sequence.

Wherein attachment of the EF-hand tag to the molecule is indirect, attachment may be mediated by a linker. A preferred linker is capable of forming covalent bonds to both the EF-hand tag and to the molecule that is to be tagged. Suitable linkers are known to those skilled in the art and include but are not limited to straight or branched-chain carbon linkers, heterocyclic carbon linkers, carbohydrate linkers and polypeptide linkers. In some embodiments, a bifunctional linker may be used that includes one functional group reactive with a pre-existing functionality on the EF-hand tag, and another group reactive with a pre-existing functionality on the molecule to be tagged.

Wherein the EF-hand tag is attached to a polypeptide or protein so as to form a fusion protein, it is preferred that the linker is a polypeptide linker. Moreover, the linker may be joined to side chain functional groups of constituent amino acids of the tag and/or the polypeptide or to the alpha amino and carboxyl groups of the terminal amino acids of the EF-hand tag and the polypeptide that is to be tagged.

In certain embodiments, cleavable linkers may be used to attach the molecule of interest to the EF-hand tag. This allows for the EF-hand tag to be separated from the molecule of interest, for example by the addition of an agent capable of cleaving the linker. A number of different cleavable linkers are known to those of skill in the art. Such linkers may be cleaved for example, by irradiation of a photolabile bond or acid-catalyzed hydrolysis. There are also polypeptide linkers which incorporate a protease recognition site and which can be cleaved by the addition of a suitable protease enzyme.

EF-Hand Fusion Proteins

In a further aspect of the invention, provided herein are EF-hand fusion proteins. Such fusion proteins comprise an EF-hand subdomain or fragment thereof according to the embodiments described above, conjugated to a polypeptide sequence that is not part of the EF-hand subdomain or fragment thereof.

In a preferred embodiment, the EF-hand subdomain comprises the amino acid sequence of SEQ ID NO: 2 or a fragment thereof, or an amino acid sequence with at least 70%, 75%, 80%, 85%, 90%, 95% identity thereto. In a further preferred embodiment, the EF-hand subdomain comprises EF1 from calbindin D9k.

The polypeptide part of the fusion protein that is not part of the EF-hand subdomain may be any suitable polypeptide or protein sequence. In one embodiment, the polypeptide to which the EF-hand subdomain tag is attached may be a single chain variable fragment (scFv) of an immunoglobulin comprising any $V_H$ and $V_L$ domains of interest.

EF-hand fusion proteins of the present invention may be produced using either chemical synthesis techniques or using recombinant expression techniques.

Standard chemical peptide synthesis techniques are known in the art and include solid phase synthesis techniques.

Recombinant expression typically involves protein production via use of a suitable expression cassette or expression vector. Expression vectors of the present invention are designed so as to express a polypeptide or protein tagged with an EF-hand subdomain or fragment thereof.

In certain embodiments, the expression vector comprises a polynucleotide sequence encoding an EF-hand tag according to the present invention and a cloning site having one or more restriction sites (i.e. a multiple cloning site) for the insertion of a further polynucleotide sequence encoding the polypeptide or protein to be tagged with the EF-hand subdomain or fragment thereof. The cloning site should be positioned such that when the polynucleotide sequence encoding the polypeptide or protein is inserted in the vector, it is in frame with the polynucleotide sequence encoding the EF-hand tag, such that when the polynucleotide of the vector is transcribed and translated, a fusion protein is produced.

Within the expression vector, the polynucleotide encoding the EF-hand tag may be positioned upstream of downstream of the multiple cloning site such that the tag is positioned at either the 5' or 3' end of the polypeptide.

Expression vectors for the production of EF-hand fusion proteins may be bacterial plasmids or cosmids or may be yeast vectors such as yeast artificial chromosomes (YACs), which replicate as small linear chromosomes. Suitable expression vectors may also be derived from bacteriophage, including all DNA and RNA phage, or viruses such as baculoviruses, retroviruses, adenoviruses, adeno-associated viruses, Herpes viruses, Vaccinia viruses and all single-stranded, double-stranded and partially double-stranded DNA viruses, all positive and negative stranded RNA viruses, and replication defective retroviruses.

For recombinant expression of the fusion protein, the polynucleotide encoding the fusion protein should be operably linked to at least one regulatory sequence within the expression vector, wherein the regulatory sequence is capable of driving or effecting expression of the fusion protein. The term 'regulatory sequence' is to be taken in a broad context and is intended to refer to any nucleotide sequence capable of effecting expression of polynucleotides to which it is operably linked including but not limited to promoters, enhancers and other naturally-occurring or synthetic transcriptional activator elements. The regulatory sequence may be located at the 5' or 3' end of the polynucleotide sequence. The term 'operably linked' refers to a functional linkage between the regulatory sequence and the polynucleotide sequence such that the regulatory sequence drives transcription of the polynucleotide. Operably linked elements may be contiguous or non-contiguous. Preferably, the regulatory sequence is a promoter selected from the group including but not limited to constitutive promoters, inducible promoters and/or tissue specific promoters.

The EF-hand tagged fusion proteins of the present invention can be expressed in a host cell. The term "host cell" is intended to include any cell or cell line into which a recombinant expression vector for production of an EF-hand tagged fusion protein as described above may be introduced for the purposes of effecting expression. Suitable host cells include, but are not limited to bacterial cells (e.g. E. coli), yeast cells, fungal cells, plant cells, invertebrate cells and vertebrate cells including mammalian cells. The host cells should not be derived from human embryos.

The choice of expression vector and associated regulatory or promoter sequence may depend on the host cell to be used. For example, expression vectors incorporating the CMV immediate early promoter are suitable for use in mammalian host cells.

The expression vector may be transfected or transformed into a suitable host cell using any of the standard techniques known to those skilled in the art. Examples of transfection techniques include, but are not limited to, calcium phosphate precipitation, DEAE-dextran-mediated transfection, lipofection, electroporation and microinjection. The vector may be maintained as a non-integrated vector, for example a plasmid, or alternatively, may be integrated into the host cell genome.

The expression vector may optionally comprise a selectable marker gene. As used herein, the term 'selectable marker gene' includes any gene, which confers a phenotype on a cell in which it is expressed to facilitate the identification and/or selection of cells, which are transfected or transformed with an expression construct of the invention. Examples of suitable selectable markers include resistance genes against ampicillin (Ampr), tetracycline (Tcr), kanamycin (Kanr), phosphinothricin, chloramphenicol (CAT), neomycin and G418 geneticin. Other suitable marker genes provide a metabolic trait, for example manA. Visual marker genes may also be used and include for example beta-glucuronidase (GUS), luciferase and Green Fluorescent Protein (GFP).

The expression vector of the invention may further include an origin of replication which is required for maintenance and/or replication in a specific cell type or host cell. One example is when an expression construct is required to be maintained in a bacterial cell as an extra-chromosomal or episomal genetic element (e.g. a plasmid or cosmid molecule) in a cell. Preferred origins of replication include but are not limited to pUC-ori, f1-ori, pBR322 on (pMB1) and colE1 ori.

Figure 1:
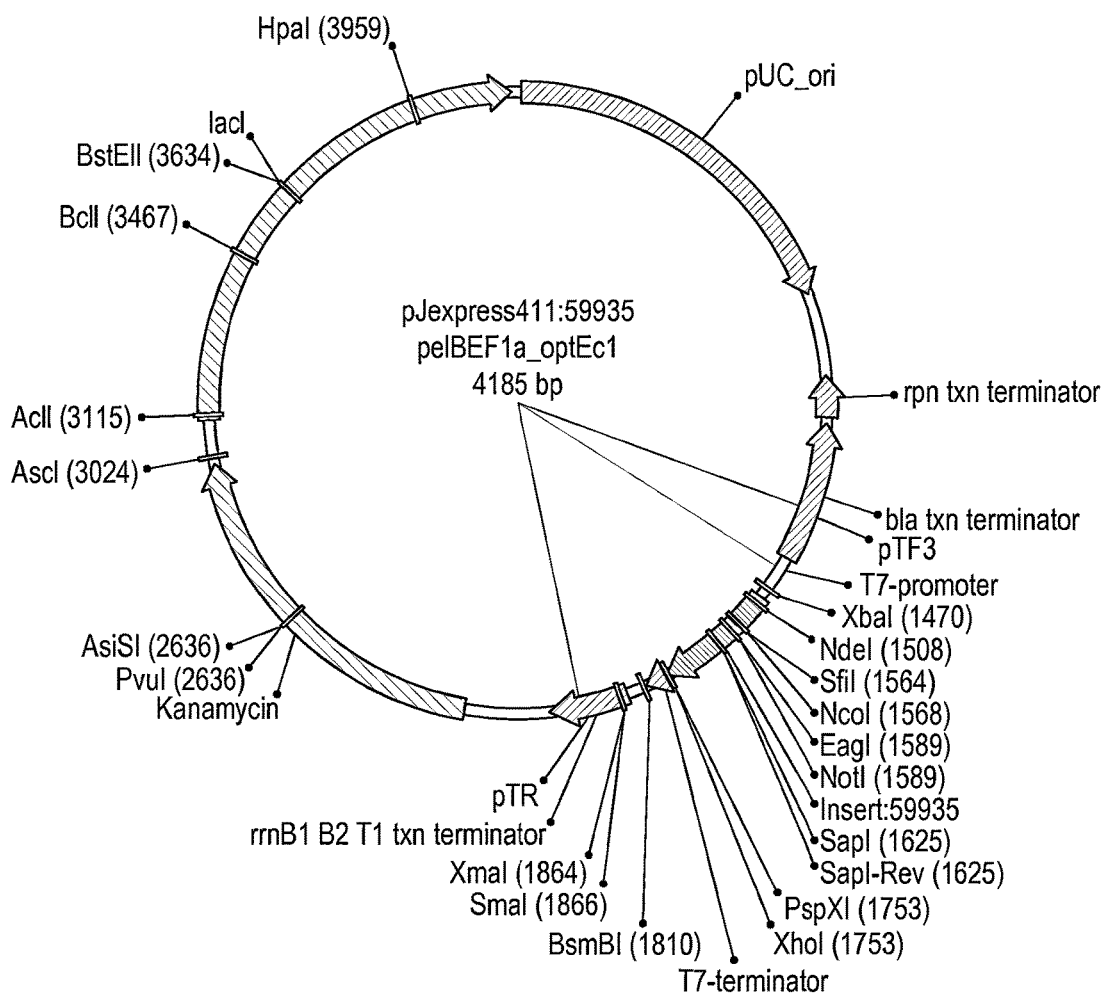
FIG. 1 Plasmid map for pJexpress-pelB-EF1.

An expression vector (pJexpress411:59935-pelBEF1a_optEc1) of the present invention is shown in FIG. 1 and the polynucleotide sequence is shown in SEQ ID NO:19. The expression vector comprises an expression cassette suitable for expression of a fusion protein incorporating the EF1 EF-hand subdomain of calbindin D9k. The expression vector incorporates a pelB leader sequence and a multiple cloning site, including the NcoI and NotI sites for insertion of a polypeptide of interest downstream of a T7 promoter. The insertion of a polypeptide allows the polypeptide to be transcribed in frame with the EF1 EF-hand subdomain of calbindin D9k (encoded by the polynucleotide sequence represented by nucleotides 1621-1746 of SEQ ID NO:19 i.e. SEQ ID NO: 31 within the vector insert at nucleotides 1496-1758 of SEQ ID NO:19 i.e. SEQ ID NO: 30). The expression vector also includes multiple restriction sites, a kanamycin resistance gene and a pUC_ori origin of replication. Full details of the features and restriction enzyme sites present in the vector shown in FIG. 1 are provided in Table 1 below.

TABLE 1

| Vector | Feature Map | Restriction Map | | |
|---|---|---|---|---|
| | | Name | Sequence | Cut Positions |
| pJexpress411:59935 (SEQ ID NO: 19) | Insert including sequence encoding calbindin D9k EF1 EF-hand subdomain: 59935 - Start: 1496 End: 1758 (SEQ ID NO: 30) | AclI | AACGTT | 3115 |
| | | AlwNI | CAGNNNCTG | 321, 1537 |
| | | ApaI | GGGCCC | 974, 3664 |
| | | ApaLI | GTGCAC | 416, 3433 |
| | EF1 sequence - Start: 1621 End: 1746 (SEQ ID NO: 31) | AscI | GGCGCGCC | 3024 |
| | | AseI | ATTAAT | 1423, 2835, 4138 |
| | pUC_ori - Start: 2 End: 805 | AsiSI | GCGATCGC | 2636 |
| | rpn txn terminator - Start: 977 End: 1090 (Complementary) | AvaI | CYCGRG | 967, 1753, 1864 |
| | | BclI | TGATCA | 3467 |
| | bla txn terminator - Start: 1097 End: 1397 (Complementary) | BglI | GCCNNNNNGGC | 978, 1564 |
| | | BsmBI | CGTCTC | 1810(C) |
| | rrnB1 B2 T1 txn terminator - Start: 1858 End: 2032 | BspHI | TCATGA | 2, 2158 |
| | | BsrBI | CCGCTC | 801, 2156, 1453(C) |
| | pTF3 - Start: 1281 End: 1306 | | | |
| | pTR - Start: 1941 End: 1957 (Complementary) | BsrDI | GCAATG | 3866, 3500(C) |
| | | BssHII | GCGCGC | 32, 3024, 3864 |
| | T7-terminator - Start: 1764 End: 1810 | BstEII | GGTNACC | 3634 |
| | T7-promoter - Start: 1424 End: 1440 | BstXI | CCANNNNNNTGG | 3255, 3384, 3507 |
| | | BtsI | GCAGTG | 2584, 4186, 2497(C), 3818(C) |
| | Kanamycin - Start: 2217 End: 3011 | | | |
| | lacI - Start: 3106 End: 4176 | EagI | CGGCCG | 1589 |
| | | EcoRV | GATATC | 1314, 3903 |
| | | HincII | GTYRAC | 1332, 3959 |
| | | HpaI | GTTAAC | 3959 |
| | | KasI | GGCGCC | 1091, 4092 |
| | | MluI | ACGCGT | 1819, 3453 |
| | | NarI | GGCGCC | 1092, 4093 |
| | | NcoI | CCATGG | 1568 |
| | | NdeI | CATATG | 1508 |
| | | NotI | GCGGCCGC | 1589 |
| | | NruI | TCGCGA | 2073, 2293 |
| | | NsiI | ATGCAT | 1388, 2486, 2752 |
| | | PciI | ACATGT | 730, 1326 |
| | | PspOMI | GGGCCC | 970, 3660 |
| | | PspXI | VCTCGAGB | 1753 |
| | | PvuI | CGATCG | 2636 |
| | | PvuII | CAGCTG | 4053, 4146 |
| | | SapI | GCTCTTC | 1625(C) |
| | | SapI-Rev | GAAGAGC | 1625 |
| | | SfiI | GGCCNNNNNGGCC | 1564 |
| | | SmaI | CCCGGG | 1866 |
| | | SspI | AATATT | 1083, 1244, 2193, 2560 |
| | | XbaI | TCTAGA | 1470 |
| | | XhoI | CTCGAG | 1753 |
| | | XmaI | CCCGGG | 1864 |

Further expression vectors according to the present invention are shown in FIGS. 4-7: pJexpress404:92688-EFTag-Nterminal-6His (FIG. 4, polynucleotide sequence in SEQ ID NO:20); pJexpress401:92689-EFTag-Cterminal-6His (FIG. 5, polynucleotide sequence in SEQ ID NO:21); pJ602:92691-EFTag-Nterminal-6His-mammalian (FIG. 6, polynucleotide sequence in SEQ ID NO:22); and pJ602:92690-EF1-Cterminal-6His-mammalian (FIG. 7, polynucleotide sequence in SEQ ID NO:23). These expression vectors also comprise an expression cassette suitable for expression of a fusion protein incorporating the EF1 EF-hand subdomain of calbindin D9k. Full details of the features and restriction enzyme sites present in the vectors shown in FIGS. 4-7 are provided in Table 2 below.

TABLE 2

| Vector | Feature Map | Restriction Map | | |
|---|---|---|---|---|
| | | Name | Sequence | Cut Positions |
| pJexpress 404:92688 (SEQ ID NO: 20) | Insert including sequence encoding calbindin D9k EF1 EF-hand subdomain: 92688 - Start: 153 End: 489 (SEQ ID NO: 24) <br> EF1 sequence - Start: 241 End: 366 (SEQ ID NO: 32) <br> pUC_ori - Start: 1102 End: 1905 (Complementary) <br> rpn txn terminator - Start: 817 End: 930 <br> rrnB1 B2 T1 txn terminator - Start: 4111 End: 4285 (Complementary) <br> pTF3 - Start: 601 End: 626 (Complementary) <br> pTR - Start: 4186 End: 4202 <br> rpo_bla_txn_term - Start: 506 End: 930 <br> T5 promoter - Start: 41 End: 88 <br> txn_terminator - Start: 506 End: 930 <br> high copy bacterial ori - Start: 1103 End: 1906 (Complementary) <br> Ampicilin - Start: 3081 End: 3929 (Complementary) <br> AmpR - Start: 3087 End: 3929 (Complementary) <br> lacI - Start: 1916 End: 2986 (Complementary) | Acc65I | GGTACC | 401 |
| | | AclI | AACGTT | 2974, 3371, 3744 |
| | | AfeI | AGCGCT | 103, 3195 |
| | | AlwNI | CAGNNNCTG | 1588 |
| | | ApaI | GGGCCC | 936, 2431 |
| | | ApaLI | GTGCAC | 1486, 2654, 3812 |
| | | AscI | GGCGCGCC | 3063 |
| | | AseI | ATTAAT | 1951, 3317 |
| | | AvaI | CYCGRG | 385, 935, 4274 |
| | | BamHI | GGATCC | 376 |
| | | BclI | TGATCA | 2620 |
| | | BglI | GCCNNNNNGGC | 495, 9313265 |
| | | BglII | AGATCT | 389 |
| | | BlpI | GCTNAGC | 475 |
| | | BspEI | TCCGGA | 3231 |
| | | BspHI | TCATGA | 44, 1900, 3980 |
| | | BsrBI | CCGCTC | 9(C), 70(C), 1105(C), 3986(C) |
| | | BsrDI | GCAATG | 2593, 2227(C) |
| | | BssHII | GCGCGC | 1870, 2223, 3063 |
| | | BstBI | TTCGAA | 269 |
| | | BstEII | GGTNACC | 2452 |
| | | BstXI | CCANNNNNN | 2588, 2711, 2840 |
| | | BstXI | TGG | |
| | | BtsI | GCAGTG | 2275, 3545, 1907(C), 3565(C) |
| | | EcoRI | GAATTC | 343 |
| | | EcoRV | GATATC | 592, 2188 |
| | | HincII | GTYRAC | 574, 2132 |
| | | HindIII | AAGCTT | 417 |
| | | HpaI | GTTAAC | 2132 |
| | | KasI | GGCGCC | 811, 1995 |
| | | KpnI | GGTACC | 405 |
| | | MluI | ACGCGT | 2634 |
| | | NarI | GGCGCC | 812, 1996 |
| | | NcoI | CCATGG | 405 |
| | | NdeI | CATATG | 170 |
| | | NheI | GCTAGC | 208 |
| | | NruI | TCGCGA | 4069 |
| | | PciI | ACATGT | 576, 1172 |
| | | PsiI | TTATAA | 83, 772 |
| | | PspOMI | GGGCCC | 932, 2427 |
| | | PstI | CTGCAG | 397 |
| | | PvuI | CGATCG | 3515 |
| | | PvuII | CAGCTG | 398, 1945, 2038 |
| | | SacI | GAGCTC | 386 |
| | | ScaI-HF | AGTACT | 3625 |
| | | SmaI | CCCGGG | 4276 |
| | | SspI | AATATT | 662, 823, 3949 |
| | | XbaI | TCTAGA | 129 |
| | | XhoI | CTCGAG | 385 |
| | | XmaI | CCCGGG | 4274 |
| | | XmnI | GAANNNNTTC | 3744 |
| pJexpress 401:92689 (SEQ ID NO: 21) | Insert including sequence encoding calbindin D9k EF1 EF-hand subdomain: 92689 - Start: 1567 End: 1888 (SEQ ID NO: 25) <br> EF1 sequence - Start: 1757 End: 1882 (SEQ ID NO: 32) <br> pUC_ori - Start: 2 End: 805 <br> rpn txn terminator - Start: 977 End: 1090 (Complementary) <br> bla txn terminator - | Acc65I | GGTACC | 1686 |
| | | AclI | AACGTT | 3166 |
| | | AfeI | AGCGCT | 1517 |
| | | AlwNI | CAGNNNCTG | 321 |
| | | ApaI | GGGCCC | 974, 3715 |
| | | ApaLI | GTGCAC | 416, 3484 |
| | | AscI | GGCGCGCC | 3075 |
| | | AseI | ATTAAT | 2886, 4189 |
| | | AsiSI | GCGATCGC | 2687 |
| | | AvaI | CYCGRG | 967, 1670, 1915 |
| | | BamHI | GGATCC | 1661 |

TABLE 2-continued

| Vector | Feature Map | Restriction Map Name | Sequence | Cut Positions |
|---|---|---|---|---|
| | Start: 1097 End: 1397 (Complementary) | BclI | TGATCA | 3518 |
| | rrnB1 B2 T1 txn terminator - Start: 1909 End: 2083 | BglI | GCCNNNNNGC | 978, 1894 |
| | pTF3 - Start: 1281 End: 1306 | BglII | AGATCT | 1674 |
| | pTR - Start: 1992 End: 2008 (Complementary) | BspHI | TCATGA | 2, 1458, 2209 |
| | T5 promoter - Start: 1455 End: 1502 | BsrBI | CCGCTC | 801, 2207, 1423(C), 1484(C) |
| | high copy bacterial ori - Start: 1 End: 804 | BsrDI | GCAATG | 3917, 3551(C) |
| | Kanamycin - Start: 2265 End: 3062 | BssHII | GCGCGC | 32, 3075, 3915 |
| | lacI - Start: 3157 End: 4227 | BstBI | TTCGAA | 1785 |
| | | BstEII | GGTNACC | 3685 |
| | | BstXI | CCANNNNNNTGG | 3306, 3435, 3558 |
| | | BtsI | GCAGTG | 2635, 4237, 2548(C), 3869(C) |
| | | EcoRI | GAATTC | 1859 |
| | | EcoRV | GATATC | 1314, 3954 |
| | | HincII | GTYRAC | 1332, 4010 |
| | | HpaI | GTTAAC | 4010 |
| | | KasI | GGCGCC | 1091, 4143 |
| | | KpnI | GGTACC | 1690 |
| | | MluI | ACGCGT | 3504 |
| | | NarI | GGCGCC | 1092, 4144 |
| | | NcoI | CCATGG | 1690 |
| | | NdeI | CATATG | 1584 |
| | | NheI | GCTAGC | 1622 |
| | | NruI | TCGCGA | 2124, 2344 |
| | | NsiI | ATGCAT | 1388, 2537, 2803 |
| | | PciI | ACATGT | 730, 1326 |
| | | PsiI | TTATAA | 1134, 1497 |
| | | PspOM1 | GGGCCC | 970, 3711 |
| | | PstI | CTGCAG | 1682 |
| | | PvuI | CGATCG | 2687 |
| | | PvuII | CAGCTG | 1683, 4104, 4197 |
| | | SacI | GAGCTC | 1671 |
| | | SmaI | CCCGGG | 1917 |
| | | SspI | AATATT | 1083, 1244, 2244, 2612 |
| | | XbaI | TCTAGA | 1543 |
| | | XhoI | CTCGAG | 1670 |
| | | XmaI | CCCGGG | 1915 |
| pJ602:92691 (SEQ ID NO: 22) | Insert including sequence encoding calbindin D9k EF1 EF-hand subdomain: 92691 - Start: 2108 End: 2444 (SEQ ID NO: 26) | AatII | GACGTC | 1599, 1652, 1735, 1921, 3182 |
| | | Acc65I | GGTACC | 2356 |
| | | AccI | GTMKAC | 3771, 3778 |
| | | AciI | AACGTT | 4113, 4486 |
| | EF1 sequence - Start: 2196 End: 2321 (SEQ ID NO: 32) | AfeI | AGCGCT | 3937 |
| | | AlwNI | CAGNNNCTG | 321 |
| | pUC_ori - Start: 2 End: 805 | ApaI | GGGCCC | 974 |
| | rpn txn terminator - Start: 977 End: 1090 (Complementary) | ApaLI | GTGCAC | 416, 3481, 4554 |
| | | AseI | ATTAAT | 1481, 2086, 2678, 3078, 4059 |
| | pTF3 - Start: 1281 End: 1306 | | | |
| | rpo_bla_txn_term - Start: 977 End: 1401 (Complementary) | AvaI | CYCGRG | 967, 2340, 3028, 3214, 3224 |
| | txn_terminator - Start: 977 End: 1401 (Complementary) | AvrII | CCTAGG | 3007 |
| | | BamHI | GGATCC | 2331 |
| | CMV promoter - Start: 1454 End: 2054 | BclI | TGATCA | 3058 |
| | | BglI | GCCNNNNNGC | 978, 1564, 1686, 1757, 3441, 4007 |
| | SV40 ori - Start: 2682 End: 3025 | BglII | AGATCT | 2344 |
| | zeocin resistance - Start: 3136 End: 3510 | BlpI | GCTNAGC | 2430 |
| | | BspEI | TCCGGA | 3973 |
| | SV40 polyadenylation signal - Start: 3638 End: 3768 | BspHI | TCATGA | 2, 4722 |
| | | BsrBI | CCGCTC | 801, 1422(C), 3190(C), 4728(C) |
| | high copy bacterial ori - Start: 1 End: 804 | BssHII | GCGCGC | 32, 3172 |
| | ZeoR - Start: 3139 End: 3501 | BstBI | TTCGAA | 2224 |
| | Ampicilin - Start: 3823 End: 4671 (Complementary) | BtsI | GCAGTG | 4287, 2062(C), 3715(C), 4307(C) |
| | AmpR - Start: 3829 End: 4671 (Complementary) | EagI | CGGCCG | 3467 |
| | | EcoRI | GAATTC | 2298 |
| | | EcoRV | GATATC | 1314 |
| | | FseI | GGCCGGCC | 3412 |
| | | HincII | GTYRAC | 1332, 1458, 3072, 3146, 3779 |

TABLE 2-continued

| Vector | Feature Map | Restriction Map Name | Sequence | Cut Positions |
|---|---|---|---|---|
| | | HindIII | AAGCTT | 2372 |
| | | KasI | GGCGCC | 1091 |
| | | KpnI | GGTACC | 2360 |
| | | MscI | TGGCCA | 3139 |
| | | NarI | GGCGCC | 1092 |
| | | NcoI | CCATGG | 1834, 2360, 2914, 3134 |
| | | NdeI | CATATG | 1708, 2125 |
| | | NgoMIV | GCCGGC | 3408, 3469, 3583 |
| | | NheI | GCTAGC | 2163 |
| | | NruI | TCGCGA | 4811 |
| | | NsiI | ATGCAT | 2757, 2829 |
| | | PciI | ACATGT | 730, 1326 |
| | | PmlI | CACGTG | 3067, 3513 |
| | | PsiI | TTATAA | 1134, 2609, 3659 |
| | | PspOMI | GGGCCC | 970 |
| | | PstI | CTGCAG | 2352 |
| | | PvuI | CGATCG | 4257 |
| | | PvuII | CAGCTG | 2353 |
| | | SacI | GAGCTC | 2042, 2341 |
| | | SalI | GTCGAC | 3777 |
| | | SalI-HF | GTCGAC | 3777 |
| | | ScaI-HF | AGTACT | 4367 |
| | | SexAI | ACCWGGT | 2774, 3299 |
| | | SmaI | CCCGGG | 3030, 3226 |
| | | SnaBI | TACGTA | 1814 |
| | | SpeI | ACTAGT | 1473 |
| | | SphI | GCATGC | 2755, 2827 |
| | | SspI | AATATT | 1083, 1244, 4691 |
| | | StuI | AGGCCT | 3006 |
| | | XhoI | CTCGAG | 2340 |
| | | XmaI | CCCGGG | 3028, 3224 |
| | | XmnI | GAANNNNTTC | 2679, 4486 |
| | | ZraI | GACGTC | 1597, 1650, 1733, 1919, 3180 |
| pJ602:92690 (SEQ ID NO: 23) | Insert including sequence encoding calbindin D9k EF1 EF-hand subdomain: 92690 - Start: 2108 End: 2429 (SEQ ID NO: 27) EF1 sequence - Start: 2298 End: 2423 (SEQ ID NO: 32) pUC_ori - Start: 2 End: 805 rpn txn terminator - Start: 977 End: 1090 (Complementary) pTF3 - Start: 1281 End: 1306 rpo_bla_txn_term - Start: 977 End: 1401 (Complementary) txn_terminator - Start: 977 End: 1401 (Complementary) CMV promoter - Start: 1454 End: 2054 SV40 ori - Start: 2667 End: 3010 zeocin resistance - Start: 3121 End: 3495 SV40 polyadenylation signal - Start: 3623 End: 3753 high copy bacterial ori - Start: 1 End: 804 ZeoR - Start: 3124 End: 3486 Ampicilin - Start: 3808 End: 4656 (Complementary) AmpR - Start: 3814 End: 4656 (Complementary) | AatII | GACGTC | 1599, 1652, 1735, 1921, 3167 |
| | | Acc65I | GGTACC | 2227 |
| | | AccI | GTMKAC | 3756, 3763 |
| | | AclI | AACGTT | 4098, 4471 |
| | | AfeI | AGCGCT | 3922 |
| | | AlwNI | CAGNNNCTG | 321 |
| | | ApaI | GGGCCC | 974 |
| | | ApaLI | GTGCAC | 416, 3466, 4539 |
| | | AseI | ATTAAT | 1481, 2086, 2663, 3063, 4044 |
| | | AvaI | CYCGRG | 967, 2211, 3013, 3199, 3209 |
| | | AvrII | CCTAGG | 2992 |
| | | BamHI | GGATCC | 2202 |
| | | BclI | TGATCA | 3043 |
| | | BglI | GCCNNNNNG | 978, 1564, 1686, 1757, 3426, 3992 |
| | | BglI | GC | |
| | | BglII | AGATCT | 2215 |
| | | BspEI | TCCGGA | 3958 |
| | | BspHI | TCATGA | 2, 4707 |
| | | BsrBI | CCGCTC | 801, 1422(C), 3175(C), 4713(C) |
| | | BssHII | GCGCGC | 32, 3157 |
| | | BstBI | TTCGAA | 2326 |
| | | BtsI | GCAGTG | 4272, 2062(C), 3700(C), 4292(C) |
| | | EagI | CGGCCG | 3452 |
| | | EcoRI | GAATTC | 2400 |
| | | EcoRV | GATATC | 1314 |
| | | FseI | GGCCGGCC | 3397 |
| | | HincII | GTYRAC | 1332, 1458, 3057, 3131, 3764 |
| | | KasI | GGCGCC | 1091 |
| | | KpnI | GGTACC | 2231 |
| | | MscI | TGGCCA | 3124 |
| | | NarI | GGCGCC | 1092 |
| | | NcoI | CCATGG | 1834, 2231, 2899, 3119 |

TABLE 2-continued

| Vector | Feature Map | Restriction Map | | |
|---|---|---|---|---|
| | | Name | Sequence | Cut Positions |
| | | NdeI | CATATG | 1708, 2125 |
| | | NgoMIV | GCCGGC | 3393, 3454, 3568 |
| | | NheI | GCTAGC | 2163 |
| | | NruI | TCGCGA | 4796 |
| | | NsiI | ATGCAT | 2742, 2814 |
| | | PciI | ACATGT | 730, 1326 |
| | | PmlI | CACGTG | 3052, 3498 |
| | | PsiI | TTATAA | 1134, 2594, 3 644 |
| | | PspOMI | GGGCCC | 970 |
| | | PstI | CTGCAG | 2223 |
| | | PvuI | CGATCG | 4242 |
| | | PvuII | CAGCTG | 2224 |
| | | SacI | GAGCTC | 2042, 2212 |
| | | SalI | GTCGAC | 3762 |
| | | SalI-HF | GTCGAC | 3762 |
| | | ScaI-HF | AGTACT | 4352 |
| | | SexAI | ACCWGGT | 2759, 3284 |
| | | SmaI | CCCGGG | 3015, 3211 |
| | | SnaBI | TACGTA | 1814 |
| | | SpeI | ACTAGT | 1473 |
| | | SphI | GCATGC | 2740, 2812 |
| | | SspI | AATATT | 1083, 1244, 4676 |
| | | StuI | AGGCCT | 2991 |
| | | XhoI | CTCGAG | 2211 |
| | | XmaI | CCCGGG | 3013, 3209 |
| | | XmnI | GAANNNNTTC | 2664, 4471 |
| | | ZraI | GACGTC | 1597, 1650, 1733, 1919, 3165 |

Once expressed, the fusion proteins may be purified according to standard procedures. In a preferred embodiment, the proteins are purified using the affinity matrix of the present invention according to the methods described below.

Methods

The affinity tag system of the present invention may be used for a variety of applications in which it is required to tether or immobilise a molecule at a substrate.

In one embodiment, the affinity tag system may be used to detect the presence of a molecule in a sample containing a mixture of molecules, for example to detect a specific biological molecule or protein in a biological sample containing many different types of biological molecule. The molecule or protein of interest is attached to an EF-hand tag of the type described above, and the sample containing the EF-hand tagged molecule or protein is then brought into contact with an affinity matrix according to any of the embodiments described above comprising the cognate EF-hand affinity ligand. Any unbound molecules are washed away leaving only bound EF-hand-tagged molecules immobilised at the substrate of the affinity matrix. Detection of bound molecules may be carried out using any suitable means known to one of skill in the art including detection of bound proteins using antibodies or antigen-binding fragments thereof capable of recognising the protein of interest.

In another embodiment, the affinity tag system of the invention may be used to generate a protein "array", such as a protein array for use in detecting the binding of a ligand or inhibitor compound to proteins of interest. Under these circumstances, the substrate of the affinity matrix may take the form of a "chip" or solid-phase array to which multiple EF-hand affinity ligands are attached. In the context of the present invention, the term 'multiple' means at least two, at least three, at least four, etc and up to at least 1000, 5000, 10,000 etc. EF-hand tagged fusion proteins of the type described above may be immobilised at the substrate via binding to the EF-hand affinity ligands attached thereto, to produce a protein array. In one embodiment, the EF-hand tagged proteins are different such that multiple proteins are displayed on the "chip" or "array" at any one time. Ligands or inhibitor compounds for testing may be applied to the protein array under suitable conditions such that ligands or inhibitor compounds with binding affinity for any of the proteins displayed are captured. Any unbound material may be washed away and any bound ligands or inhibitor compounds may be detected by techniques known to those skilled in the art.

The protein arrays described above may be modified so as to display different sets of proteins depending on the required application. For example, a first set of EF-hand tagged proteins attached to the affinity matrix may be detached by the addition of a suitable releasing agent. Suitable releasing agents include any agents capable of disrupting the interaction between the EF-hand tag of the proteins and the EF-hand affinity ligand of the affinity matrix. Once the EF-tagged proteins are detached from the matrix, the matrix may be re-loaded with a different set of EF-hand tagged proteins. In this way, affinity matrices of the invention in the form of chips or arrays coated with EF-hand affinity ligands may be recycled so as to produce different protein arrays for subsequent use.

In a preferred embodiment, the affinity tag system of the present invention may be used to purify molecules, such as biological molecules, tagged with an EF-hand subdomain or fragment thereof from a sample. In a particularly preferred embodiment, the affinity tag system is used to purify proteins or polypeptides from a sample. In a first step, the molecule or protein of interest is tagged with an EF-hand tag as described above. In a second step, a sample containing an EF-hand tagged molecule of interest is brought into contact with an affinity matrix comprising an EF-hand subdomain or fragment thereof attached to a substrate. The EF-hand subdomain or fragment thereof of the affinity matrix, i.e. the EF-hand affinity ligand, must be capable of binding the EF-hand tag attached to the molecule of interest.

The sample containing the EF-hand tagged molecule of interest is brought into contact with the affinity matrix under conditions that permit binding of the EF-hand tag and the EF-hand affinity ligand. The EF-hand tagged molecule to be purified is generally contacted with the affinity matrix in a solution or buffer that includes calcium ions (or another ion or other equivalent that can substitute for calcium) to facilitate binding of the tagged molecule to the matrix. Binding of the EF-hand tagged molecule may occur at calcium concentrations exceeding 10 nM. In the presence of calcium, the $K_D$ for the binding of the EF-hand subdomains or fragments thereof will typically be less than 1 µM, preferably less than 100 nM and more preferably less than 10 nM.

Any unbound material in the sample can be removed, for example by washing of the affinity matrix. In a final step, the molecule of interest may be released from the affinity matrix using any suitable releasing agent. Generally, using methods of the invention, a substantially pure composition of at least 80%, 85%, 90%, 95% 98% or 99% homogeneity is obtained.

The releasing agent may be any agent capable of separating the molecule of interest from the affinity matrix. In one embodiment, the releasing agent is an agent capable of disrupting the interaction between the EF-hand tag and the EF-hand affinity ligand of the matrix. Suitable agents for this purpose include agents capable of sequestering or chelating calcium. Calcium chelators are well known to those of skill in the art and include, but are not limited to, EDTA, EGTA, desferal, biphosphonate, 1,2-bis(2-aminophenoxy) etane-N,N,N'N'-tetraacetic acid (BAPTA), BAPTA/AM, EGTA/AM, 5N-BAPTA, 5,5'Br$_2$-BAPTA, fura-2, Quin-2 and the like.

In an alternative or in some cases, additional embodiment, the releasing agent is an agent capable of cleaving the molecule of interest from the EF-hand tag such that the molecule of interest is detached from the affinity matrix. As described above, the EF-hand tag may be attached to the molecule of interest via a cleavable linker. Wherein the molecule of interest is a polypeptide or protein attached to the EF-hand tag via a polypeptide linker, the polypeptide linker may be engineered so as to contain a protease recognition site. Any protease capable of recognising the cleavage site of the polypeptide linker may be used to release the protein of interest from the EF-hand tag and thereby detach the protein of interest from the affinity matrix.

For the methods of affinity purification described herein, the affinity matrix may take any suitable form. For example, the affinity matrix may occupy the interior of an affinity purification column to which a sample is applied. Any unbound material may be separated from the bound EF-tagged proteins by washing of the column.

In a preferred embodiment, the affinity matrix comprises a substrate of nanoparticles, in particular silica nanoparticles, with EF-hand affinity ligands attached. The sample containing the EF-hand tagged proteins is mixed with the nanoparticles under conditions that permit binding between the EF-hand subdomains. The EF-hand tagged molecules bound to the nanoparticles may be collected by centrifugation under conditions suitable for specifically pelleting the nanoparticles. Various washing steps may be employed to improve the purity of the protein preparation, as would be readily understood by one skilled in the art.

In a further application, the affinity tag system of the invention may be used to achieve targeted delivery of molecules of interest. In one embodiment, the affinity tag system may be used to target the delivery of drugs to particular sites within the body of a patient to be treated. Under these circumstances, the substrate of the affinity matrix may comprise a targeting agent, for example an antibody, or antigen binding fragment thereof, capable of recognising an antigen present within a particular tissue or on a particular cell within the body. The affinity matrix would thus be localised to a particular site within the body. The EF-hand tag could be attached to any molecule or drug intended for administration to a patient. The EF-hand tagged molecule or drug, once administered to the patient, would thus be localised to the site of the affinity matrix via the interaction with the cognate EF-hand affinity ligand. This approach may be used in particular, to target relatively non-specific or toxic drugs to their site of action and thereby reduce the overall dose needed for administration to a patient.

Kits

The components of the affinity system described herein may be packaged in kit form. For example, provided herein is a kit comprising an affinity matrix according to any of the embodiments described above. Also provided herein is a kit comprising an expression vector of the invention suitable for the production of an EF-hand tagged fusion protein according to the present invention.

The kits may optionally include labelling and or instructional materials providing directions for practicing the methods of the invention.

The invention will be further understood with reference to the following non-limiting examples.

EXAMPLES

1. Production of an EF-Hand Fusion Protein—scFv-EF1

The variable heavy gene, glycine serine linker sequence and the variable light chain gene sequence was excised from anti-ubiquitin scFv clone (Tomlinson I library, MRC Gene resource) using the restriction sites Nco l/Not l. The excised fragment was gel purified and ligated into the pJexpress411:59935-pelBEF1a optEc1 cloning vector (pJexpress-pelB-EF1, FIG. 1) which had been digested with the Nco l/Not l restriction sites and gel purified. The ligation mixture was used to transform chemically competent E. coli BL21 cells. An overnight culture of E. coli BL21 transformed with pJExpress pelB-anti-ubiquitin scFv-EF1 was prepared by picking a single colony of the transformed bacteria into 2 ml 2×TY/100 µg/mL ampicillin/2% (w/v) glucose. The overnight culture was used to inoculate 2 liters of 2×TY/100 µg/mL ampicillin/0.1% (w/v) glucose which was grown in a 37° C. shaking incubator until it achieved an OD$_{600\ nm}$ of approx. 1.0. IPTG (Sigma) was added to a final concentration of 1 mM to induce expression of the scFv-EF1 fusion protein and the expression culture was transferred to a 30° C. shaking incubator set at 250 rpm. Following a 4 h incubation, the bacteria were pelleted by centrifugation at 4000 g for 20 min. Fifty mL of ice cold periplasmic extraction buffer (30 mM Tris-HCl, pH 8.0, 20% (w/v) sucrose, 1 mM EDTA) were then added to the bacterial pellets for resuspension. The bacteria were centrifuged again at 4000 g for 20 min and the supernatant was retained. Fifty mL of ice cold osmotic shock buffer (5 mM MgSO$_4$) were then added to the bacterial pellets. The preparation was again centrifuged at 4000 g for 20 min and the supernatant was retained. Supernatants from the periplasmic extraction and osmotic shock extraction were pooled and centrifuged at 17,500 g for 20 min to remove cellular debris.

2. Production of an EF-Hand Affinity Matrix 1 mg of 70 nm $SiO_2$—COOH nanoparticles (5 mg/ml) was pelleted in a microcentrifuge at 10,000 RPM for 5 minutes. Equal volumes of 0.1 M NHS and 0.4 M EDC were first mixed, and 100 µl of the mixture was used to re-suspend the nanoparticles. The EDC/NHS was removed from the nanoparticles after a brief spin (5 min) at 10,000 RPM in a microcentrifuge. 100 microliters of a PDEA solution, made by dissolving 4.5 mg PDEA in 205 µl 0.1M borate buffer at pH 8.5, was used to resuspend the particles to introduce a reactive disulphide group onto carboxyl groups of the carboxylated nanoparticles. The nanoparticles were pelleted once more and the supernatant removed. EF2-GGC at 0.1 mg/ml in 100 µl 10 mM sodium formate buffer at pH 4.3 was then used to resuspend the particles and left to incubate for 10 minutes. The C-term Cys of EF2-GGC was used to create a covalent link between the immobilized EF2-GGC on the nanoparticle surface. Deactivation of the excess reactive disulphides on the nanoparticle surface was done by resuspending the pelleted particles in 200 µl of 50 mM L-cysteine with 1 M NaCl in 100 mM formate buffer at pH 4.3. The resulting EF2-$SiO_2$ nanoparticles were reconstituted in 10 mM Tris HCl, 1 mM CaCl2, 150 mM KCl.

3. Protein Purification of scFv-EF1 Using EF-Hand Affinity Tag System

Figure 2:
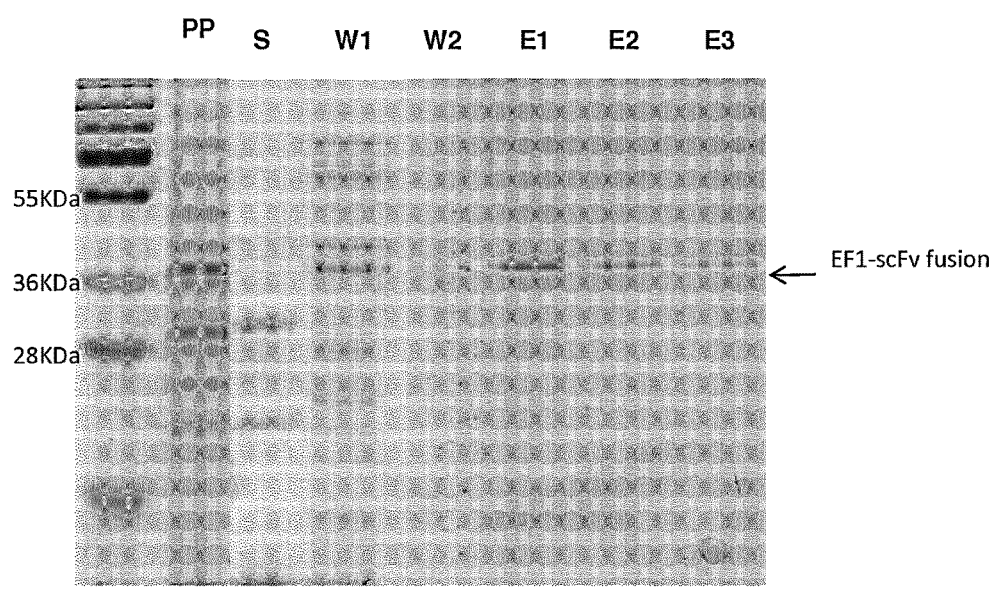
FIG. 2 Proof of concept experiment for novel EF2-SiO$_2$ nanoparticle protein purification method—expression and purification of EF1-scFv fusion protein from pelBEF1. (PP) periplasmic fraction of lysate from pelB-scFv-EF1 expressing E. coli (S) supernatant post-incubation with EF2-SiO$_2$ nanoparticles (W1) supernatant post-wash 1 with calcium containing wash buffer (W2) supernatant post-wash 2 with calcium containing wash buffer (E1) supernatant post-wash with calcium free EDTA elution buffer (E2) supernatant post-wash with calcium free EDTA elution buffer (E3) supernatant post-wash with calcium free EDTA elution buffer.

Pooled supernatants from the periplasmic extraction and osmotic shock extraction were buffer exchanged in 10 mM Tris-HCl, 1 mM $CaCl_2$, 150 mM KCl pH7.4 using a centriprep YM-10 cartridge with centrifugation at 3,000×g. 1 ml of the exchanged preparation was then incubated with 0.1 mg/ml EF2-$SiO_2$ nanoparticles on a rotary shaker, rotating for at least 1 hour at room temperature. The mixture was then spun at 10,000 RPM in a microcentrifuge for 10 minutes. The supernatant was removed and saved. The nanoparticle mixture was then washed twice in 150 µl of calcium wash buffer (10 mM Tris-HCl, 1 mM $CaCl_2$, 150 mM KCl pH7.4). The nanoparticles were then eluted two or three times in 150 µl of EDTA elution buffer (10 mM Tris-HCl, 1 mM EDTA, pH8.0). The resulting fractions (supernatants, washes and eluates) were analysed by electrophoresis on a 10% polyacrylamide gel and visualisation by Coomassies staining and destaining (FIG. 2).

4. Production of EF1-Snap25 Fusion Protein from pEF1-N

The coding sequence for human synaptosomal-associated protein, 25 kDa (SNAP25) (accession number: NM_130811) was amplified from a vector construct using gene specific PCR cloning primers:—

```
Snap25-BamHI
                                      (SEQ ID NO: 28)
TGG GGA TCC ATG GCC GAA GAC Snap25-NcoI
                                      (SEQ ID NO: 29)
ATC CCA TGG TTA ACC ACT TCC CAG
```

The PCR product was digested with BamHI and NcoI restriction enzymes that cut within restriction sites incorporated into the cloning primer sequences. The digested PCR product was purified and ligated into the multiple cloning sequence of pEFTag-N terminal expression vector (pEF1-N, FIG. 4) that had been digested with the same restriction enzymes and gel purified. Briefly, 1 µl of T4 DNA Ligase was added to a 2:1 ratio of gene insert to vector in a 20 µl reaction for 10 minutes. 5 µl of this ligation reaction was used to transform competent *E. coli* BL21 Rosetta cells and a single transformed colony was picked and inoculated into 5 ml of Overnight Express Autoinduction Media (Novagen) and grown for 8 hours at 37° C. from which 2 ml was used to inoculate 100 ml of culture media. After 16 hours of growth the cells were pelleted and proteins were purified under denaturing or native conditions. Briefly denaturing preparation involved the lysis of bacterial pellets with lysis buffer containing 8M Urea with subsequent purification on Ni-NTA agarose beads on a pH gradient from pH8 to pH4.5. Native purification was performed by suspension of bacterial pellets in a Tris buffer with 300 mM NaCl and sonication of cells with a sonicator microtip at 60 W.

5. Protein Purification of EF1-Snap25 Using EF-Hand Affinity Tag System

EF1-Snap25 was purified from cleared bacterial lysate following incubation of 1 ml of native lysate with 0.1 mg/ml EF2-$SiO_2$ nanoparticles on a rotary shaker, rotating for at least 1 hour at 4° C. The mixture was then spun at 10,000 RPM in a microcentrifuge for 10 minutes. The supernatant was removed and saved. The nanoparticle mixture was then washed twice in 150 µl of calcium wash buffer (10 mM Tris-HCl, 1 mM $CaCl_2$, 150 mM KCl pH7.4). The nanoparticles were then eluted twice in 250 µl of EDTA elution buffer (10 mM Tris-HCl, 1 mM EDTA, pH8.0). The resulting fractions (supernatants, washes and eluates) were analysed by electrophoresis as shown in FIG. 3A.

EF1-Snap25 was also purified using the 6×His sequence incorporated into the EF1-N vector sequence. Using immobilised metal affinity chromatography and Ni-NTA agarose beads the EF1-Snap25 protein was purified by incubating 5 ml of native lysate with 1 ml Ni-NTA agarose slurry (approximately 0.25-0.5 g/ml) and placing in a chromatography column. The column was washed in 10-20 mM imidazole containing buffer followed by elution in 1 ml native lysis buffer containing 250 mM imidazole. This purification protocol was performed as a positive control for the purification of EF1-Snap25 via the EF1-EF2 protocol. The results are shown in FIG. 3B.

CONCLUSION

Figure 3:
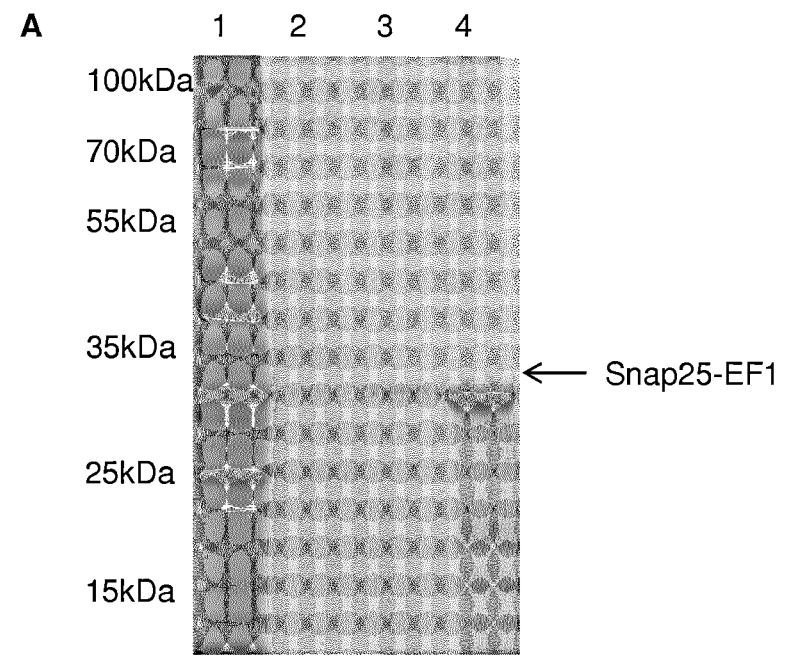
FIG. 3 Proof of concept experiment for novel EF2-SiO$_2$ nanoparticle protein purification method—expression and purification of EF1-Snap25 fusion protein from pEF1-N.
Figure 3:
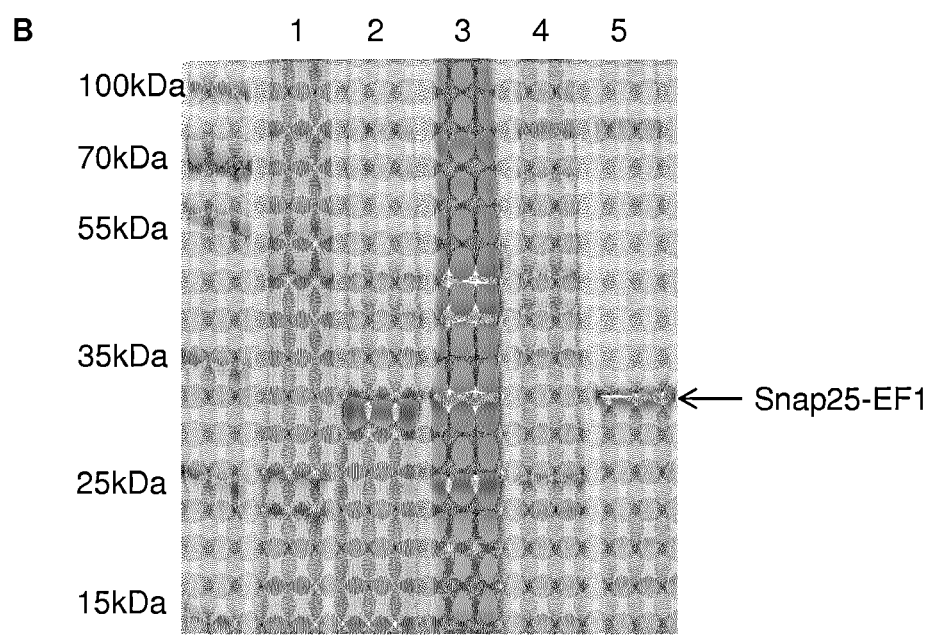

The EF-hand affinity tag system facilitated a significantly more rapid purification protocol than His tag purification, with the centrifugation-based recovery facilitating purification of protein in a significantly shorter timeframe than the immobilised metal affinity chromatography employed with the His tag method. The recovery of protein was also significantly better using the EF-hand affinity tag system requiring very little affinity matrix (i.e., EF2-nanoparticles) to purify equivalent amounts of protein as is shown in FIG. 3. As a consequence, a much higher purity was achieved in a much shorter timeframe.

Importantly for sensitive proteins, the EDTA elution of protein is a much more gentle treatment than the imidazole elution protocol used for His-tagged proteins. Using the EF-hand affinity tag system, very often the resulting protein preparation will not require dialysis whereas this is a prerequisite with imidazole eluted His-tagged protein. In summary, there is a significant advantage using the EF-hand affinity tag system in terms of speed of purification, yield of purified protein and optimum condition of the protein.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. An affinity tag system for immobilizing a molecule, said system comprising:

(i) an affinity matrix comprising a first EF-hand subdomain or fragment thereof covalently attached to a substrate wherein the substrate is selected from solid or porous beads, or is packed into a column, a capillary, a microcapillary or an electrophoresis tube; and (ii) a molecule tagged with a second EF-hand subdomain or fragment thereof, wherein the molecule is immobilized at the substrate via the interaction between the first and second EF-hand subdomains or fragments thereof;

wherein the first EF-hand subdomain or fragment thereof is capable of binding to the second EF-hand subdomain or fragment thereof in the presence of calcium with an affinity of binding ($K_D$) between the first EF-hand subdomain and the second EF-hand subdomain of 1 nM or less; and wherein the first EF-hand subdomain or fragment thereof comprises SEQ ID NO:1 or an amino acid sequence having at least 85% sequence identity thereto and the second EF-hand subdomain or fragment thereof comprises SEQ ID NO:2 or an amino acid sequence having at least 85% sequence identity thereto, or wherein the first EF-hand subdomain or fragment thereof comprises SEQ ID NO:2 or an amino acid sequence having at least 85% sequence identity thereto and the second EF-hand subdomain or fragment thereof comprises SEQ ID NO:1 or an amino acid sequence having at least 85% sequence identity thereto.

2. The system of claim 1 wherein the substrate of the affinity matrix is selected from the group consisting of cross-linked polysaccharide, ceramic, metal, glass, plastic, cellulose, and silica.

3. The system of claim 1 wherein the first EF-hand subdomain is attached to the substrate via random amine coupling and/or wherein the first EF-hand subdomain is modified so as to facilitate attachment to the substrate and/or wherein the first EF-hand subdomain is attached to the substrate via a linker.

4. The system of claim 1 wherein the molecule is a biological molecule.

5. The system of claim 1 wherein the molecule tagged with a second EF-hand subdomain or fragment thereof is a fusion protein comprising a second EF-hand subdomain and a polypeptide sequence that is not part of the EF-hand subdomain.

6. An affinity matrix comprising a first EF-hand subdomain or fragment thereof that is capable of binding to a second EF-hand subdomain or fragment thereof in the presence of calcium, wherein said first EF-hand domain or fragment thereof is covalently attached to a substrate wherein the substrate is selected from solid or porous beads, or is packed into a column, a capillary, a microcapillary or an electrophoresis tube, wherein the affinity of binding ($K_D$) between the first EF-hand subdomain and the second EF-hand subdomain in the presence of calcium is 1 nM or less; and wherein the first EF-hand subdomain or fragment thereof comprises SEQ ID NO:1 or an amino acid sequence having at least 85% sequence identity thereto and the second EF-hand subdomain or fragment thereof comprises SEQ ID NO:2 or an amino acid sequence having at least 85% sequence identity thereto, or wherein the first EF-hand subdomain or fragment thereof comprises SEQ ID NO:2 or an amino acid sequence having at least 85% sequence identity thereto and the second EF-hand subdomain or fragment thereof comprises SEQ ID NO:1 or an amino acid sequence having at least 85% sequence identity thereto.

7. The matrix of claim 6 wherein the substrate of the affinity matrix is selected from the group consisting of cross-linked polysaccharide, ceramic, metal, glass, plastic, cellulose, and silica.

8. The matrix of claim 6 wherein the first EF-hand subdomain or fragment thereof is attached to the substrate via random amine coupling or wherein the first EF-hand subdomain or fragment thereof is modified so as to facilitate attachment to the substrate, or wherein the first EF-hand subdomain or fragment thereof is attached to the substrate via a linker.

9. A method for purifying a biological molecule tagged with an EF-hand subdomain or a fragment thereof from a sample, said method comprising the steps of:
(i) providing the affinity matrix of claim 6;
(ii) bringing a sample containing the tagged biological molecule into contact with the affinity matrix of (i) under conditions that permit binding of the EF-hand subdomains;
(iii) separating any unbound material from the tagged biological molecule bound to the affinity matrix; and
(iv) effecting release of the tagged biological molecule from the affinity matrix by adding an agent that chelates calcium or by cleavage of the EF-hand subdomain tag.

10. The method of claim 9 wherein the affinity matrix comprises an EF-hand domain attached to a substrate comprising, consisting essentially of or consisting of silica nanoparticles and/or wherein the biological molecule is a protein or polypeptide.

11. The system of claim 1 wherein the substrate comprises silica nanoparticles.

12. The system of claim 4 wherein the biological molecule is selected from a protein, a polypeptide, a nucleic acid, a lipid, a polysaccharide, a carbohydrate, and a lectin.

13. The system of claim 5 wherein the second EF-hand subdomain is attached to the polypeptide sequence at the N-terminus of the polypeptide sequence.

14. The matrix of claim 6 wherein the substrate comprises silica nanoparticles.

15. The system of claim 5 wherein the second EF-hand subdomain is attached to the polypeptide sequence at the C-terminus of the polypeptide sequence.

16. The system of claim 5 wherein the second EF-hand subdomain is attached to an amino acid residue of the polypeptide sequence at a position between the N-terminus and C-terminus of the polypeptide sequence.

17. The system of claim 5 wherein the second EF-hand subdomain is attached to the polypeptide sequence via a linker.

* * * * *

UNITED STATES PATENT AND TRADEMARK OFFICE
CERTIFICATE OF CORRECTION

PATENT NO. : 9,676,872 B2
APPLICATION NO. : 14/369331
DATED : June 13, 2017
INVENTOR(S) : David O'Connell et al.

It is certified that error appears in the above-identified patent and that said Letters Patent is hereby corrected as shown below:

On the Title Page

(73) Assignee:
"Northwestern University, Evanston IL" should be replaced by "University College Dublin, Dublin, Ireland".

Signed and Sealed this
Fifth Day of September, 2017

Joseph Matal
*Performing the Functions and Duties of the*
*Under Secretary of Commerce for Intellectual Property and*
*Director of the United States Patent and Trademark Office*